(12) United States Patent
Zhang et al.

(10) Patent No.: US 8,105,798 B2
(45) Date of Patent: Jan. 31, 2012

(54) CYTOPLASMIC ACTIVITY OF RETINOID X RECEPTOR AND ITS REGULATION BY LIGANDS AND DIMERIZATION

(75) Inventors: Xiao-kun Zhang, San Diego, CA (US); Xihua Cao, San Diego, CA (US); Wen Liu, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 433 days.

(21) Appl. No.: 10/918,116

(22) Filed: Aug. 13, 2004

(65) Prior Publication Data
US 2005/0054008 A1 Mar. 10, 2005

Related U.S. Application Data

(60) Provisional application No. 60/494,842, filed on Aug. 13, 2003.

(51) Int. Cl.
*G01N 33/53* (2006.01)
(52) U.S. Cl. ................................ 435/7.8; 435/7.95
(58) Field of Classification Search .................. None
See application file for complete search history.

(56) References Cited

U.S. PATENT DOCUMENTS

| | | | |
|---|---|---|---|
| 5,625,048 A | 4/1997 | Tsien et al. |
| 5,777,079 A | 7/1998 | Tsien et al. |
| 5,804,387 A | 9/1998 | Cormack et al. |
| 6,458,926 B1 | 10/2002 | Evans et al. |
| 6,506,917 B1 | 1/2003 | Evans et al. |

FOREIGN PATENT DOCUMENTS
WO WO 01/28532 * 4/2001

OTHER PUBLICATIONS

Casas et al., FASEB J. 17: 426-436, 2003.*
Huang et al., Cancer Res. 61: 6918-6924, 2001.*
Li, J. Biol., Chem. 276: 38152-38158, 2001.*
Liu et al., World J. of Gastroenterology, 8: 446-450, 2002.*
Aarnisalo, P., et al., J. Biol. Chem., 277: 35118-35123 (2002).
Bissonnette, R. P., et al., Mol. Cell Biol., 15: 5576-5585 (1995).
Bourguet, W., et al., Nature, 375: 377-382 (1995).
Bourguet, W., et al., Mol. Cell, 5: 289-298 (2000).
Chang, C., et al., J. Steroid Biochem., 34: 391-395 (1989).
Davis, I. J., et al, Mol. Endo., 7: 953-964 (1993).
Dawson, M. I., et al., Cancer Res., 61: 4723-4730 (2001).
Defranco, D. B., Cell Biochem. Biophys., 30: 1-24 (1999).
Egea, P. F., et al., EMBO J., 19: 2592-2601 (2000).
Elbashir, S. M., et al., Nature 411: 494-498 (2001).
Fahrner, T. J., et al., Mol. Cell. Biol., 10: 6454-6459 (1990).
Forman, B. M., et al., Cell, 81: 541-550 (1995).
Gampe, R. T., Jr., et al., Mol. Cell, 5: 545-555 (2000).
Gampe, R. T., Jr., et al., Genes Dev., 14: 2229-2241 (2000).
Hazel, T. G. et al., Mol. Cell Biol., 11: 3239-3246 (1991).
Hazel, T. G., et al., PNAS, 85: 8444-8448 (1988).
Hadvat, C. V. and Irving, S. G., Mol. Endo., 9: 1692-1700 (1995).
Heyman, R. A., et al., Cell 68: 397-406 (1992).
Holmes, W. F., et al., J. Biol. Chem., 277: 45408-45419 (2002).
Kastner, P., et al., Cell, 83: 859-869 (1995).
Katagiri, Y., et al., Nature Cell Biol., 2; 435-440 (2000).
Kousteni, S., et al., Cell, 104: 719-730 (2001).
Kudo, N., et al., PNAS, 96: 9112-9117(1999).
Labelle, Y., et al., Oncogene, 18: 3303-3308 (1999).
Law, S. W., et al., Mol. Endo., 6: 2129-2135 (1992).
Lee, J. M., et al., PNAS, 99: 11878-11883 (2002).
Levin, A., et al., Nature, 355: 359-361 (1992).
Li, H., et al., Science, 289: 1159-1164 (2000).
Li, H., et al., Mol. Cell. Biol., 18: 4719-4731 (1998).
Lin, B., et al., Mol. Cell Biol., 20: 957-970 (2000).
Liu, Z. G., et al., Nature, 367: 281-284 (1994).
Mages, H. W., et al., Mol. Endo., 8: 1583-1591 (1994).
Mangelsdorf, D. J., et al., Cell, 83: 841-850 (1995).
Masuyama, N., et al., J. Biol. Chem., 276: 32799-32805 (2001).
Migliaccio, A., et al., EMBO J., 19: 5406-5417 (2000).
Milbrandt, J., J. Neuron, 1: 183-188 (1988).
Ohkura, N., et al., Biochem. Biophys. Res. Commun., 205: 1959-1965 (1994).
Pekarsky, Y., et al., PNAS, 98: 3690-3694 (2001).
Perlmann, T. and Jansson, L., Genes Dev. 9: 769-782 (1995).
Philips, A., et al., Mol. Cell Biol., 17: 5946-5951 (1997).
Sacchetti, P., et al. J. Biol. Chem., 277: 35088-35096 (2002).
Sakaue, M., et al., Cell Death Differ., 8: 411-424 (2001).
Simoncini, T., et al., Nature 407: 538-541 (2000).
Szondy, Z., et al.; Cell Death Differ, 5: 4-10 (1998).
Uemura, H., and Chang, C., Endocrinology, 139: 2329-2334 (1998).
Wansa, K. D., et al., J. Biol. Chem., 277: 33001-33011 (2002).
Weih, F., et al., PNAS, 93: 5533-5538 (1998).
Wen, W., et al., Cell, 82: 463-473 (1995).
Wilson, T. E., et al., Science 252: 1296-1300 (1991).
Woronicz, J. D., et al., Mol. Cell Biol., 15: 6364-6376 (1995).
Wu, Q., et al., Mol. Cell Biol., 17: 6598-6608 (1997).
Wu, Q., et al., EMBO J., 16: 1656-1669 (1997).
Wu, Q., et al., Oncogene, 21: 3925-3933 (2001).
Xu, L., et al., Curr. Opin. Genet. Dev., 9: 140-147 (1999).
Yang, Y., et al., PNAS, 92: 3051-3055 (1995).
Yang, Y., et al., J. Biol. Chem., 270: 18672-18677 (1995).
Yang, Y. et al., PNAS, 90: 6170-6174 (1993).
Zhang, X. K., et al., Nature, 355: 441-446 (1992).
Zhang, X. K., et al., Nature, 358: 587-591 (1992).
Zhang, X. K., et al., Mol. Cell. Biol., 14: 4311-4323 (1994).
Zhang, X. K., et al., Receptor, 3: 183-191 (1992).
Mader, S., et al., "The patterns of binding of RAR, RXR and TR homo- and heterodimers to direct repeats are dictated by the binding . . . ," EMBO J., (1993), 12(13): 5029-5041.

(Continued)

*Primary Examiner* — Gyan Chandra
(74) *Attorney, Agent, or Firm* — Knobbe Martens Olson & Bear LLP

(57) ABSTRACT

This invention relates to methods for identifying agents useful for treatment of diseases and pathological conditions affected by Retinoid X Receptor apoptosis. The invention also relates to methods for treating diseases and pathological conditions affected by RXR apoptosis. The invention includes compositions that are useful in the study and treatment of diseases and pathological conditions affected by RXR apoptosis.

20 Claims, 13 Drawing Sheets

OTHER PUBLICATIONS

Database Geneseq [Online], "Human RXR ligand binding domain HsRXR-truncatedEF," (2002), Accession No. AAU10273.
Database Geneseq [Online], "Human RXRalpha protein in DNA binding domain," (2003), Accession No. AAE30398.
Database Geneseq [Online], "Human nuclear receptor NUR77 protein sequence," (2002), Accession No. AAU96997.

* cited by examiner

CYTOPLASMIC ACTIVITY OF RETINOID X RECEPTOR AND ITS REGULATION BY LIGANDS AND DIMERIZATION

RELATED APPLICATION

Benefit of priority under 35 U.S.C. 119(e) is claimed herein to U.S. Provisional Application No. 60/494,842, filed Aug. 13, 2003. The disclosure of the above referenced application is incorporated by reference in its entirety herein.

STATEMENT ON FEDERALLY SPONSORED RESEARCH

This invention was made in part with United States government support under grant number NIH CA87000, DAMD17-01-1-0172, DAMD17-01-1-0032 awarded by the National Institutes of Health and the US ARMY. The U.S. government has certain rights in this invention.

FIELD OF THE INVENTION

This invention relates to screening methods for identifying agents useful for treating apoptosis related diseases and pathological conditions and to compositions having an improved therapeutic profile identified using such screening methods.

BACKGROUND OF THE INVENTION

Compounds having retinoid-like activity are well known in the art, and are described in numerous United States and other patents and in scientific publications. It is generally known and accepted in the art that retinoid-like activity is useful for treating animals of the mammalian species, including humans, to cure or alleviate the symptoms and conditions of numerous diseases and conditions. Thus, pharmaceutical compositions having a retinoid-like compound or compounds as the active ingredient are useful as treatments and/or cures of a variety of disorders. Retinoid compounds are also useful for preventing and treating cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma, modulation of apoptosis, including both the induction of apoptosis and inhibition of T-Cell activated apoptosis and metabolic disorders, such as type 2 diabetes, hyperlipidemia and atherosclerosis.

It is also general knowledge in the art that two main types of retinoid receptors exist in mammals (and other organisms). The two main types or families of receptors respectively designated the Retinoic Acid Receptors (RAR) and Retinoid X Receptors (RXR). Within each type there are subtypes; in the RAR family the subtypes are designated RAR.alpha., RAR.beta. and RAR.gamma., in RXR the subtypes are: RXR.alpha., RXR.beta. and RXR.gamma.

RXRs belonging to the nuclear receptor superfamily consist of a large number of ligand-regulated transcription factors that mediate the diverse physiological functions of steroid hormones, retinoids, thyroid hormone, and vitamin D in embryonic development, growth, differentiation, apoptosis, and homeostasis (Kastner, P., et al., Cell 83, 859-869 (1995); Mangelsdorf, D. J., et al., Cell 83, 841-850 (1995)). The superfamily also includes many orphan receptors whose ligands remain to be identified. All nuclear receptors consist of three domains: the N-terminal domain with varying length, the well conserved DNA binding domain (DBD) and the ligand binding domain (LBD) (Kastner, P., et al., Cell 83, 859-869 (1995); Mangelsdorf, D. J., et al., Cell 83, 841-850 (1995); Heyman, R. A., et al. Cell 68, 397-406 (1992).; Levin et al., Nature 355, 359-361 (1992)). The LBD is responsible for receptor dimerization and its interaction with transcriptional coactivators or corepressors. RXRs mediate retinoid signaling through the RXR/RAR heterodimer and the RXR/RXR homodimers (Kastner, P., et al., Cell 83, 859-869 (1995); Mangelsdorf, D. J., et al., Cell 83, 841-850 (1995); Zhang, X. K., et al., Nature 358, 587-591 (1992b)). In addition, RXRs form heterodimers with many members of the subfamily 1 nuclear receptors, including vitamin D receptor (VDR), peroxisome proliferator-activated receptor (PPAR), and thyroid hormone receptor (TR), as well as several orphan receptors, such as liver X receptor (LXR), pregnane X receptor (PXR), constitutively activated receptor (CAR), and TR3/Nur77/NGFI-B (Kastner, P., et al., Cell 83, 859-869 (1995); Mangelsdorf, D. J., et al., Cell 83, 841-850 (1995)). RXRs, therefore, play an essential role in the regulation of multiple nuclear hormone signaling pathways through their unique and potent heterodimerization capacity.

The role of RXR in regulating transcriptional activation of its heterodimerization partners has been extensively studied (Kastner, P., et al., Cell 83, 859-869 (1995); Mangelsdorf, D. J., et al., Cell 83, 841-850 (1995); Zhang, X. K., et al., Nature 358, 587-591 (1992b)). RXR homodimerization and its heterodimerization are required for efficient DNA binding and transactivation. In the absence of ligands, some nuclear receptors repress transcription of target genes through their interaction with transcriptional corepressors. Ligand binding causes a conformational change of receptors, allowing dissociation of transcriptional corepressors and association of transcriptional coactivators (Xu, L., et al., Curr Opin Genet Dev 9, 140-147 (1999)). However, whether RXR acts nongenotropically to regulate important biological processes remains unknown.

Orphan receptor TR3 (also known as nur77 and NGFI-B) (Chang, C., et al. J Steroid Biochem 34, 391-395 (1989); Hazel, T. G., et al. Natl Acad Sci USA 85, 8444-8448 (1988); Milbrandt, J Neuron 1, 183-188 (1988)) is an immediate-early response gene whose expression is rapidly induced by a variety of extracellular stimuli, including growth factors, phorbol ester and cAMP-dependent pathways. TR3 and its closely related family members, Not-1 (also called Nurr1 and RNR-1) (Law et al., 1992; Mages et al., 1994) and NOR-1 (also called MINOR and TEC) (Hedvat, C. V., et al., Mol Endocrinol 9, 1692-1700 (1995); Ohkura, N., et al., Biochem Biophys Res Commun 205, 1959-1965 (1994)) constitute a distinct subfamily within the nuclear receptor superfamily (Kastner, P., et al., Cell 83, 859-869 (1995); Mangelsdorf, D. J., et al., Cell 83, 841-850 (1995); Zhang, X. K., et al., Nature 358, 587-591 (1992b)). TR3 was originally recognized for its role in cell proliferation and differentiation. Paradoxically, TR3 was later found to be a potent pro-apoptotic molecule (Maruyama, K., et al., Cancer Lett 96, 117-122 (1995)).

TR3 functions in the nucleus as a transcription factor to regulate gene expression necessary to alter the cellular phenotype in response to various stimuli. TR3 response elements (NBRE or NurRE) have been identified (Philips, A., et al., Mol Cell Biol 17, 5946-5951 (1997); Wilson, T. E., et al., Science 252, 1296-1300 (1991)). In addition, it has been shown that TR3 can form a heterodimer with RXR (Forman, B. M., et al. Cell 81, 541-550 (1995); Perlmann and Jansson, Genes Dev 9, 769-782 (1995)), and that TR3 can interact with orphan receptor COUP-TF (Wu et al., Embo J 16, 1656-1669 (1997b)), which binds to the RAR.beta. promoter and is required for efficient RAR.beta. expression (Lin et al., Mol Cell Biol 20, 957-970 (2000)). Through its interaction with RXR and COUP-TF, TR3 modulates RAR.beta. expression and alters the growth response of cells to retinoids (Wu et al., Embo J 16, 1656-1669 (1997b)).

One well-established apoptotic pathway involves mitochondria (Green and Reed, Science 281: 1309-1312 (1998); Green and Kroemer, Trends Cell Biol 8, 267-271(1998)). Cytochrome c is exclusively present in mitochondria and is released from mitochondria in response to a variety of apoptotic stimuli. Expression of TR3 is rapidly induced during apoptosis of immature thymocytes and T-cell hybridomas as well as various types of cancer cells (Li, H., et al. Science 289, 1159-1164 (2000); Li, H., et al., Mol Cell Biol 18, 4719-4731 (1998); Liu, Z. G., et al., Nature 367, 281-284 (1994); Uemura, H., and Chang, C. Endocrinology 139, 2329-2334 (1998); Woronicz, J. D., et al., Nature 367, 277-281 (1994)). Overexpression of a dominant-negative TR3 protein or inhibition of TR3 expression by antisense TR3 inhibited apoptosis, whereas constitutive expression of TR3 results in massive apoptosis (Li, H., et al. Science 289, 1159-1164 (2000); Li, H., et al., Mol Cell Biol 18, 4719-4731 (1998); Liu, Z. G., et al., Nature 367, 281-284 (1994); Uemura, H., and Chang, C. Endocrinology 139, 2329-2334 (1998); Weih et al., 1996; Woronicz, J. D., et al., Nature 367, 277-281 (1994); Woronicz et al., 1995). Recent studies have demonstrated that TR3 acts outside the nucleus to mediate several important biological functions, including apoptosis and differentiation. TR3 translocates from the nucleus to the cytoplasm in response to NGF treatment of PC 12 phaeochromocytoma cells, thus facilitating NGF-induced PC12 cell differentiation. TR3, in response to apoptotic stimuli, translocates from the nucleus to the cytoplasm where it targets mitochondria to induce cytochrome c release (Li, H., et al. Science 289, 1159-1164 (2000)). Induction of cytochrome c release is mediated by a direct interaction of TR3 with Bcl-2, which converts Bcl-2 from a protector to a killer (Li et al., Cell 116, 527-540 (2004)). Thus, in addition to its action in the nucleus, TR3 plays a diverse biological role in the cytoplasm.

Accordingly there is a need for the establishment of new RXR pathways in order to discover and develop therapeutic agents that can act on the RXR mediated pathways.

SUMMARY OF THE INVENTION

Accordingly there is a need for the discovery and development of therapeutic agents that can act through RXR. The development of such compounds relies upon the discovery of RXR pathways that regulate important biological processes, such as apoptosis. Inventor has discovered that a new RXR pathway involves the migration of RXR.alpha. from the nucleus to the cytoplasm. By combining an understanding of the molecular basis for this new RXR pathway with appropriate screening methodologies it is possible to discover compounds that selectively modulate one or more of the functions regulated by the RXR pathway.

Inventor has discovered that RXR can interact with a number of cytoplasmic proteins and that the binding of certain agents to RXR can initiate the migration of RXR from the nucleus of a cell to the cytoplasm where such interactions may take place. RXR's interaction with cytoplasmic targets can induce activity of RXR which is independent of the transcriptional regulatory activity of RXR including the induction of apoptosis in a cell. Inventor has discovered that agents such as 15-Deoxy-.delta.sup.12,14-prostaglandin J.sub.2 (15d-PGJ.sub.2), certain non-steroidal anti-inflammatory agents (such as diclofenac, sulindac and indomethacin), and others can bind to RXR and induce RXR to migrate to the cytoplasm from the nucleus of a cell. These agents induce activity of RXR that is independent from the transcriptional regulation activity of RXR.

Accordingly, Inventor has invented new screening methodologies to identify novel compounds that are selected based on their ability to modulate the migration of RXR from the nucleus to the cytoplasm of a cell, methodologies to identify novel compounds that are selected based on their ability to modulate the migration of RXR from the nucleus of a cell to the cytoplasm.

Inventor has also discovered that the formation of certain heterodimers can induce RXR to migrate from the nucleus to the cytoplasm of a cell. Inventor has discovered that the RXR/TR3 heterodimer that is formed in response to apoptotic stimuli is conformationally distinct from the RXR/TR3 heterodimers that exist within the nucleus to facilitate DNA transcription.

Inventor has discovered that certain RXR conformations can induce RXR to migrate from the nucleus to the cytoplasm of a cell. The RXR conformations facilitating such translocation can be induced by some RXR legends, including, but not limited to sulindac sulfide.

Inventor has further discovered that the RXR/TR3 heterodimer that forms in response to apoptotic stimuli migrates from the nucleus to the cytoplasm by way of CRM1-dependent export. Such export is facilitated by a nuclear export sequence (NES) present on helix seven of RXR's C-terminal end, and which can facilitate CRM 1-dependent nuclear export only when the RXR/TR3 heterodimer is in the apoptosis induced conformation.

Moreover, Inventor has discovered that the unique RXR.alpha. NES activity in the RXR.alpha./TR3 heterodimer is regulated by RXR ligand binding. Consistently, certain RXR ligands (rexinoids), such as 9-cis-RA, effectively inhibit mitochondrial localization of RXR.alpha./TR3 heterodimer and apoptosis, whereas other RXR ligands, such as sulindac sulfide and 15d-PGJ.sub.2, promote the targeting.

Inventor has thus discovered a novel nongenotropic role that RXR.alpha. plays in regulating apoptosis, and has demonstrated a complex regulation of RXR.alpha.'s sub-cellular localization by rexinoids and dimerizations.

Inventor has further invented new screening methodologies to identify novel compounds that are selected based on their ability to modulate the formation of a unique RXR-TR3 heterodimer, the migration of said heterodimer from the nucleus to the mitochondria, the targeting of the mitochondria by said heterodimer, and the subsequent facilitation of apoptosis. Such modulators would be predicted to activate, inhibit, enhance, reduce or otherwise modulate apoptosis.

Inventor has further invented new screening methodologies to identify novel compounds that are selected based on their ability to induce RXR nuclear export.

Accordingly in one embodiment, the present invention includes methods to identify compounds that act to induce the migration of RXR from the nucleus of a cell to the cytoplasm and allow RXR to interact with cytoplasmic targets.

In another embodiment, the present invention includes methods to identify compounds that act to activate, enhance, reduce, inhibit, reverse, disrupt or otherwise modulate the formation of a unique RXR/TR3 heterodimer.

In another embodiment, the present invention includes methods to identify compounds that act to activate, enhance, reduce, inhibit, reverse, disrupt or otherwise modulate the formation of a unique RXR conformation.

In another embodiment, the present invention includes methods to identify compounds that act to activate, enhance, reduce, inhibit or otherwise modulate the migration of a unique RXR/TR3 heterodimer from the nucleus to the mitochondria.

In another embodiment, the present invention includes methods to identify compounds that act to activate, enhance, reduce, inhibit or otherwise modulate the migration of RXR.

In another aspect, the present invention provides modulators discovered by the methods of the present invention for screening test compounds, methods of using such modulators, as well as pharmaceutical compositions containing such modulators that are useful for the abnormalities and disease conditions associated with apoptosis.

Thus, RXR may represent an ideal molecular target for developing cancer therapeutic drugs. Still further, RXR/TR3 heterodimers represent an ideal molecular target for developing therapeutic drugs for cancers and diseases. Additionally, the RXR cytoplasmic action, such as the RXR/TR3 apoptotic pathway, represents an ideal target for developing therapeutic drugs for cancers and diseases.

DETAILED DESCRIPTION OF THE INVENTION

Figure 1:
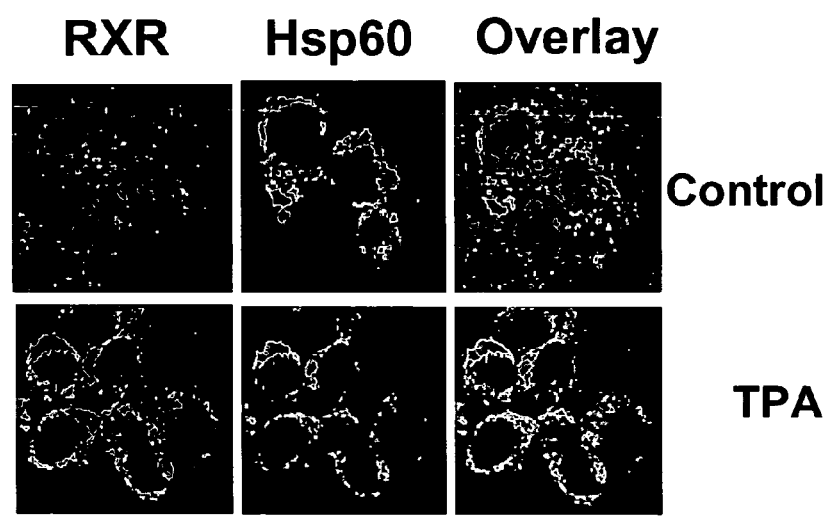
FIG. 1 illustrates the results of confocal microscopy analysis, showing mitochondrial localization of RXR in response to apoptotic stimuli.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document, as well as: Maniatis et al., Molecular Cloning: A Laboratory Manual (1989), 2nd Ed., Cold Spring Harbor, N.Y.; and Berger and Kimmel, Methods in Enzymology, Volume 152, Guide to Molecular Cloning Techniques (1987), Academic Press, Inc., San Diego, Calif., which are incorporated herein by reference. Oligonucleotides can be synthesized on an Applied Bio Systems oligonucleotide synthesizer according to specifications provided by the manufacturer. The procedures are believed to be well known in the art and are provided for the convenience of the reader. All the information contained therein is incorporated herein by reference.

As used herein, "antisense" refers to single, double or triple stranded polynucleotides and peptide nucleic acids (PNAs) that bind RNA transcript or DNA. Oligonucleotides derived from the transcription initiation site of the gene, e.g., between positions -10 and +10 from the start site, are a particular example. Triplex forming antisense can bind to double strand DNA thereby inhibiting transcription of the gene. Antisense molecules are typically 100% complementary to the sense strand but may be "partially" complementary in which only some of the nucleotides bind to the sense molecule (less than 100% complementary, e.g., 95%, 90%, 80%, 70% and sometimes less). Antisense molecules include and may be produced by methods including transcription from a gene or chemically synthesized (e.g., solid phase phosphoramidite synthesis). Antisense polynucleotides may be modified in order to provide resistance to degradation when administered to a patient. Particular examples include 5' and 3' linkages that are resistant to endonucleases and exonucleases present in various tissues or fluids in the body of an animal. Antisense polynucleotides do not require expression control elements to function in vivo. Such antisense molecules can be absorbed by the cell or enter the cell via passive diffusion. Antisense may also be introduced into a cell using a vector, such as a virus vector. However, antisense may be encoded by a nucleic acid so that it is transcribed, and, further, such a nucleic acid encoding an antisense may be operatively linked to an expression control element for sustained or increased expression of the encoded antisense in cells or in vivo.

The term "detectable label" refers to any moiety that can be selectively detected in a screening assay. Examples include without limitation, radiolabels, (e.g., .sup.3H, .sup.14C, .sup.35S, .sup.125I, .sup.131I), affinity tags (e.g. biotin/avidin or streptavidin, binding sites for antibodies, metal binding domains, epitope tags, FLASH binding domains—See U.S. Pat. Nos. 6,451,569; 6,054,271; 6,008,378 and 5,932,474—glutathione or maltose binding domains) fluorescent or luminescent moieties (e.g. fluorescein and derivatives, GFP, rhodamine and derivatives, lanthanides etc.), and enzymatic moieties (e.g. horseradish peroxidase, beta.-galactosidase, .beta.-lactamase, luciferase, alkaline phosphatase). Such detectable labels can be formed in situ, for example, through use of an unlabeled primary antibody which can be detected by a secondary antibody having an attached detectable label.

The term "DNA-binding domain" or "DBD" refers to protein domain capable of binding to a specific DNA sequence, and comprising at least one zinc finger sequence.

As used herein, the term "disrupt" embraces test compounds that cause substantially complete disassociation (i.e. greater than 90% dissociation) of formed RXR-TR3 heterodimer. The term "substantially disrupt" embraces test compounds which cause at least 50% dissociation of bound co-factor from a receptor.

As used herein, the term "functionally expressed" refers to a coding sequence which is transcribed, translated, post-translationally modified (if relevant), and positioned in a cell such that the protein provides the desired function. With reference to a reporter cassette, functional expression generally means production of a sufficient amount of the encoded cell surface reporter protein to provide a statistically significant detectable signal to report transcriptional effects of a reporter polynucleotide.

As used herein, the term "LBD" or "ligand-binding domain" refers to the protein domain of a nuclear receptor, such as a steroid superfamily receptor or other suitable nuclear receptor as discussed herein, which binds a physiological ligand and thereupon undergoes a conformational change and/or altered intermolecular interaction with an associated protein so as to confer a detectable activity upon a second, linked functional domain.

As used herein, the term "modulator" refers to a wide range of test compounds, including, but not limited to natural, synthetic or semi-synthetic organic molecules, proteins, oligonucleotides antisense and RNAi, that directly or indirectly influence the migration of RXR from the nucleus of a cell to the cytoplasm of a cell. Furthermore, the precursor of a modulator (i.e., a compound that can be converted into a modulator) is also considered to be a modulator. Similarly, a compound which converts a precursor into a modulator is also considered to be a modulator.

"Naturally fluorescent protein" refers to proteins capable of forming a highly fluorescent, intrinsic chromophore either through the cyclization and oxidation of internal amino acids within the protein or via the enzymatic addition of a fluorescent co-factor. Typically such chromophores can be spectrally resolved from weakly fluorescent amino acids such as tryptophan and tyrosine. Endogenously fluorescent proteins have been isolated and cloned from a number of marine species including the sea pansies *Renilla reniformis, R. kollikeri* and *R. mullerei* and from the sea pens *Ptilosarcus, Stylatula* and *Acanthoptilum*, as well as from the Pacific Northwest jellyfish, *Aequorea victoria*; Szent-Gyorgyi et al. (SPIE conference 1999), D.C. Prasher et al., Gene, 111:229-233 (1992) and red and yellow fluorescent proteins from coral. A variety of mutants of the GFP from *Aequorea victoria* have been created that have distinct spectral properties, improved brightness and enhanced expression and folding in mammalian cells compared to the native GFP, (*Green Fluorescent Proteins*, Chapter 2, pages 19 to 47, edited Sullivan and Kay, Academic Press, U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type proteins and are preferred for use as reporter genes in the present invention. Preferred naturally fluorescent proteins include without limitation, EGFP, YFP, Renilla GFP and DS red.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. A structural gene (e.g., a HSV tk gene) which is operably linked to a polynucleotide sequence corresponding to a transcriptional regulatory sequence of an endogenous gene is generally expressed in substantially the same temporal and apoptosis-specific pattern as is the naturally-occurring gene.

As used herein, the term "non-steroidal anti-inflammatory agents" refers to compounds which work in limiting inflammation by inhibiting the production of prostaglandins. These compounds are known to exert anti-inflammatory, analgesic and antipyretic actions. A contrast is made with steroidal compounds (such as hydrocortisone or prednisone) which also exert anti-inflammatory activity. Examples of non-steroidal anti-inflammatory agents include the COX2 inhibitors such as indomethacin, diclofenac, celecoxib naproxen, ibuprofen and rofecoxib.

As used herein, the term "nucleic acid" or "nucleotide sequence" can include an anti-sense nucleotide sequence, an RNA molecule, or an aptamer sequence. For example, a nucleotide sequence, such as an aptamer, can bind to RXR or to one or more components of a RXR/TR3 or RXR/Agent complex and modulate the level or stability of that complex. Aptamers are nucleic acid sequences that have three dimensional structures capable of binding small molecular targets including metal ions, organic dyes, drugs, amino acids, cofactors, aminoglycosides, antibiotics, nucleotide base analogs, nucleotides and polypeptides (Jayasena, S. D., Clinical Chemistry 45:9, 1628-1650, (1999)). Nucleotide sequences can be modified by several methods known in the art in order to increase the stability of these nucleotide sequences within cells.

As used herein, "orphan receptors" are members of the nuclear receptor superfamily for which no natural ligand (hormone) have yet been identified.

As used herein the term "peptidomimetic" refers to a non peptide compound that is a topological analog of the corresponding polypeptide. Such a peptidomimetic can, for example, retain some or all of the functional groups of the amino acids shown to be functionally important in the polypeptide. A peptidomimetic can also, for example, consist partially or completely of a non peptide backbone used in the art in the design of other peptidomimetics, such as a glucose scaffold, a pyrrolidinone scaffold, a steroidal scaffold, a benzodiazepine scaffold, or the like. Peptidomimetics can provide various advantages over polypeptides, and can be useful for oral administration since they can be stable when administered to a subject during passage throughout the digestive tract. In addition, peptidomimetics can be designed to allow for better penetration of the blood brain barrier (BBB).

As used herein, "RNAi" refers to small interfering double-stranded RNA molecules for use in RNA interference methods. RNA interference (RNAi) is a process of sequence-specific gene silencing by post-transcriptional RNA degradation, which is initiated by double-stranded RNA (dsRNA) homologous to a sequence of the silenced gene. A particular example of a double-stranded RNA (dsRNA) contains sense and antisense strands of about 21 contiguous nucleotides corresponding to the target gene that hybridize with 19 RNA nucleotides, leaving overhangs of two nucleotides at each 3' end (Elbashir et al., Nature 411:494-498 (2001); Zamore, Nat. Struct. Biol. 8:746-750 (2001)). dsRNAs of about 25-30 nucleotides have also been used for RNAi (Karabinos et al., Proc. Natl. Acad. Sci. USA 98:7863-7868 (2001). dsRNA can be synthesized in vitro and introduced into a cell by methods known in the art. By such methods, translation of the target polypeptide can be decreased.

A "reporter gene" includes any gene that directly or indirectly produces a specific reporter gene product, detectable label, enzymatic moiety, or cellular phenotype, such as drug resistance that can be used to monitor transcription of that gene. Preferred reporter genes include proteins with an enzymatic activity that provides enzymatic amplification of gene expression such as .beta.-lactamase, luciferase, .beta.-galactosidase, catalytic antibodies and alkaline phosphatase. Other reporter genes include proteins such as naturally fluorescent proteins or homologs thereof, cell surface proteins or the native or modified forms of an endogenous gene to which a specific assay exists or can be developed in the future. Preferred reporter genes for use in the present invention provide for multiplexed analysis.

"Selectively induced" as used herein, refers to the shift of a cell population from a non-apoptotic state to an apoptotic state. Preferably, said shift is a detectable increase in apoptosis, more preferably said shift is a 10% increase in apoptosis, most preferably said shift is a 50% increase in apoptosis.

"Treating" or "treatment" as used herein covers the treatment of a disease-state associated with apoptosis activity as disclosed herein, and includes:
 a) preventing a disease-state associated with apoptosis activity from occurring;
 b) inhibiting a disease-state associated with apoptosis activity, i.e., arresting its development; or
 c) relieving a disease-state associated with apoptosis activity, i.e., causing regression of the condition.

The term "transcription activation domain" is used herein to refer to a protein, or protein domain with the capacity to enhance transcription of a structural sequence in-trans. The ability to enhance transcription may affect the inducible transcription of a gene, or may effect the basal level transcription of a gene, or both. For example, a reporter polynucleotide may comprise a minimal-promoter driving transcription of a sequence encoding a reporter gene. Such a reporter polypeptide may be transferred to a nuclear receptor-responsive cell line for use in the creation of a modified host cell. Cloned sequences that silence expression of the reporter gene in cells cultured in the presence of an apoptosis agonist also may be included (e.g., to reduce basal transcription and ensure detectable inducibility). Numerous other specific examples of transcription regulatory elements, such as specific minimal promoters and response elements are known to those of skill in the art and may be selected for use in the methods and polynucleotide constructs of the invention on the basis of the practitioner's desired application. Literature sources and published patent documents, as well as GenBank and other sequence information data sources can be consulted by those of skill in the art in selecting suitable transcription regulatory elements and other structural and functional sequences for use in the invention. Where necessary, a transcription regulatory element may be constructed by synthesis (and ligation, if necessary) of oligonucleotides made on the basis of available sequence information (e.g., GenBank sequences for a UAS, response element, minimal promoter etc).

The term "Type I and/or Type II" refers to the conformation of the RXR:TR3 heterodimer. Type I heterodimer is in the conformation wherein said heterodimer is localized to the nucleus and is capable of binding DNA response elements. Type II heterodimer is in the conformation wherein said heterodimer is capable of migrating from the nucleus to the cytoplasm, and is further capable of associating with the mitochondria and triggering apoptosis.

As used herein, the phrase "system" refers to an intact organism or a cell-based system containing the various components required for analyzing RXR or the RXR/TR3 heterodimer cellular pathway in response to the test compounds described herein.

As applied to polypeptides, the term "substantial identity" means that two peptide sequences, when optimally aligned, such as by the programs GAP or BESTFIT using default gap weights, share at least 90 percent sequence identity, preferably at least 95 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

Since the list of technical and scientific terms cannot be all encompassing, any undefined terms shall be construed to have the same meaning as is commonly understood by one of skill in the art to which this invention belongs. Reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Inventor has discovered that RXR can be induced to migrate from the nucleus of a cell by a variety of agents and that such migration can be targeted to non-nuclear cell targets (or cytoplasmic targets) including, but not limited to the mitochondria or IkB complex (IKK). Once RXR is outside of the nucleus of the cell, RXR interacts with these non-nuclear cell targets, and this interaction induces various cell pathways such as apoptosis. These cytoplasmic actions of RXR are distinct from the traditional activities of RXR in regulating gene expression through its DNA binding activity within the nucleus.

Inventor has further discovered novel binding sites on RXR receptor and TR3 receptor, which facilitates the formation of a unique heterodimer in the nucleus in response to apoptotic stimuli. Said heterodimer is then exported from the nucleus, due in part to a nuclear export sequence that applicant discovered at the c-terminus of RXR, and once outside of the nucleus, the RXR/TR3 heterodimer targets the mitochondria wherein apoptosis is initiated. As is detailed below, the present discovery lends itself to the screening methods of the current inventions, thereby allowing for the discovery, identification and subsequent pharmaceutical formulation of compounds useful in modulating said discovery, and in turn in treating or preventing associated conditions.

In Inventor's discovery, cells provide at least a Type I and Type II RXR/TR3 heterodimer or an RXR monomer, or an RXR monomer and a TR3 monomer; a nuclear export mechanism; and a mitochondrial organelle capable of undergoing apoptosis. Preferably, said cells are mammalian cell-lines, more preferably cancer cell-lines, and most preferably LNCaP cell-lines.

Also in Inventors discovery, the sub-cellular localization, and thus the migration, of RXR is determined using techniques well known in the art. While those of ordinary skill in the art will use a variety of these as well as other well known techniques to accomplish the spirit of the current invention, Inventor preferably uses immunostaining, immunoblotting assays, detectable labels, and/or naturally fluorescent proteins operably linked to proteins and peptides of interest and uses microscopy visualization techniques.

Thus, Inventor has discovered a method for screening agents that modulate the migration of Retinoid X Receptor (RXR) from the nucleus to a non-nuclear cell target, comprising: providing a cell containing RXR located in the nucleus of said cell; incubating said cell in the presence or absence of a test agent; and selecting those agents that modulate the migration of RXR to said non-nuclear cell target.

Inventor has further discovered a method of screening for agents that modulate RXR/TR3 Type II heterodimer facilitated apoptosis, comprising: providing a cell that includes a mitochondrial associated Bcl-2 family member, and that is capable of forming an RXR/TR3 heterodimer Type I and Type II; incubating said cell in the presence or absence of a test agent; and selecting those agents that selectively induce the formation of a Type II heterodimer.

Inventor has further discovered a method for screening agents that modulate the migration of Retinoid X Receptor (RXR) and TR3 from the nucleus to a non-nuclear cell target, comprising: providing a cell containing RXR and TR3 located in the nucleus of said cell; incubating said cell in the presence or absence of a test agent; and selecting those agents that modulate the migration of RXR and TR3 to said non-nuclear cell target.

Inventor has further discovered a treatment for a variety of conditions wherein regulating programmed cell death is desired, said treatment uses agents that facilitate the cellular localization of RXR.alpha. either in its monomeric, homodimeric or heterodimeric form.

Inventor has further discovered the nucleotide and amino acid sequences of the nuclear exportation sequence and the TR3 binding domain of RXR.alpha. Similarly, Inventor has discovered the nucleotide and amino acid sequence of the RXR.alpha. binding domain of TR3.

RXR Localizes to the Mitochondria in Response to Apoptotic Stimuli.

In the pathway of the current discovery, RXR is localized to the mitochondria in response to apoptosis inducing stimuli.

For example, cells such as LNCaP prostate cancer cells are induced to apoptosis using agents such as the phorbol ester, TPA (12-0-tetradecanolphorbol 13-acetate, Cell Signaling Technology Cat. No.: 9905). Inventor has determined the sub-cellular localization of RXR.alpha. in the presence and absence of apoptosis inducing agents using many techniques well known in the art, including immunostaining with an anti-RXR primary antibody followed by a Cy-3 conjugated secondary antibody, and using confocal microscopy for visualization. Immunostaining for RXR.alpha. showed that it predominantly resides in the nucleus in the absence of TPA treatment; however, when cells were treated with TPA, RXR.alpha. was found in the cytoplasm. (FIG. 1).

Inventor has further discovered that RXR.alpha. associates with mitochondria in the presence of an apoptosis inducing agent. In the current example, RXR.alpha. association with the mitochondria is shown by staining the cells for a mitochondrial specific protein, and overlaying the staining patterns with those of RXR.alpha. For example, heat shock protein 60 (Hsp60) is a mitochondrial specific protein. LNCaP cells that have been treated with TPA are first immunostained with either anti-RXR.alpha. antibody or with anti-Hsp60 antibody. The treated cells are then incubated with a conjugated secondary antibody and visualized using confocal microscopy. In this example, Cy-3 or FITC conjugated secondary antibodies were used for visualizing the sub-cellular localization of RXR.alpha. or Hsp60, respectively. Overlaying the images reveals that the distribution patterns of Hsp60 overlaid extensively with those of RXR.alpha., revealing that RXR.alpha. associates with mitochondria in response to apoptotic stimuli. (FIG. 1).

Thus, the sub-cellular localization of RXR is varied in response to apoptotic stimuli.

Non-Steroidal Anti-Inflammatory Agents Induce the Migration of RXR from the Nucleus to Mitochondria.

Non-steroidal anti-inflammatory agents are a class of compounds that block eicosanoid production through the inhibition of prostaglandin (cyclooxygenase (COX)) activity. In addition to their general use as inhibitors of inflammation, pain, and fever, non-steroidal anti-inflammatory agents have other pharmacological effects, including inhibition of the trsnscriptional factor NF-kB that is critically involved in the expression of several inflammatory genes and the activation of peroxisome proliferator-activated receptor gamma (PPAR-.gamma.). Recently, non-steroidal anti-inflammatory agents have been shown to have an emerging utility as chemotherapeutics for the prevention and treatment of human cancer.

A large volume of studies have now demonstrated that non-steroidal anti-inflammatory agents may exert some of their cellular action through COX-independent mechanisms. Among these potential targets of NSAIDs is the peroxisome proliferator-activated receptor (PPAR) family of nuclear receptors that function as ligand-dependent transcriptional factors. PPAR.gamma. has been shown to be activated by the synthetic antidiabetic thiazolidinediones and prostaglandin D and J derivatives. However, the function of PPAR.gamma. in the setting of human cancer is controversial.

Figure 11:
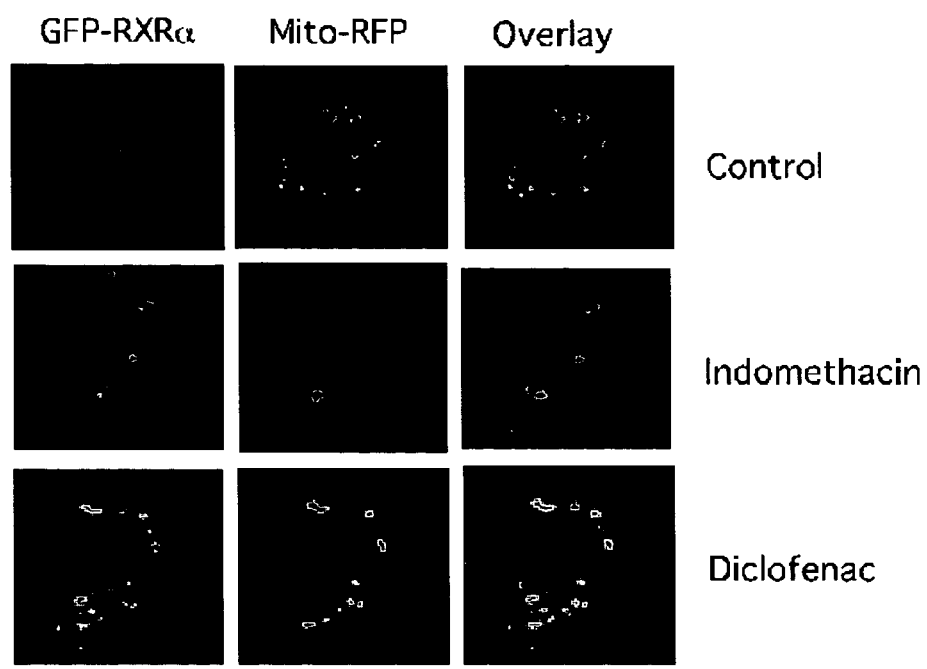
FIG. 11 is a series of confocal microscope images of immunostained cells illustrating that non-steroidal anti-inflammatory agents indomethacin and diclofenac are capable of inducing the migration of RXR.alpha. from the nucleus to the cytoplasm. Cos7 cells were transfected with GFP-RXR.alpha. and Mito-REP, and treated with or without 10.sup.-4 M indomethacin or diclofenac for 4 hours. The distribution of GFP-RXR.alpha. and Mito-REP was visualized by confocal microscopy.

Inventor has examined whether COX2 inhibitors could act through an RXR pathway. A GFP-RXR.alpha. expression vector was transfected into COS-7 cells and GFP-RXR.alpha. was expressed. Cells were then treated with indomethacin or diclofenac, which are potent apoptosis inducers. In the absence of treatment, the GFP-RXR.alpha. was localized in the nucleus; however, when cells were treated with either indomethacin or diclofenac, GFP-RXR.alpha. was found in the cytoplasm, displaying punctate patterns. The punctate distribution patterns of GFP-RXR.alpha. suggests that it may associated with cellular organelle. To study whether GFP-RXR.alpha. associated with mitochondria, a fusion containing the red fluorescent protein (RFP) fused with a mitochondrial targeting sequence (Mito-RFP) was cotransfected into cells. The distribution pattern of GFP-RXR.alpha. extensively overlays with that of Mito-RFP in cells treated with either indomethacin or diclofenac, indicating that GFP-RXR.alpha. associated with mitochondria. Thus, COX2 inhibitors indomethacin and diclofenac are capable of inducing the migration of RXR.alpha. from the nucleus to the cytoplasm. (FIG. 11).

In Response to Apoptotic Stimuli. RXR is Localized to the Mitochondria and is Mutually Dependent on TR3 Localization.

It is known that similar treatment of cancer cells with an apoptotic stimulus also results in mitochondrial localization of TR3. (H. Li et al., Science 289, 1159-64 (2000); M. Sakaue et al., Cell Death Differ 8, 411-24 (April, 2001); M. I. Dawson et al., Cancer Res 61, 4723-30. (2001); J. M. Lee et al., S. D. Hayward, Proc Natl Acad Sci USA 99, 11878-83 (Sep. 3, 2002); Q. Wu et al., Carcinogenesis 23, 1583-92 (October, 2002)). Thus, through Inventor's current discovery it is determined that both RXR.alpha. and TR3 associate with mitochondria in response to apoptotic stimuli. Furthermore, the mitochondrial association by both RXR.alpha. and TR3 are mutually dependent upon each other.

Figure 2:
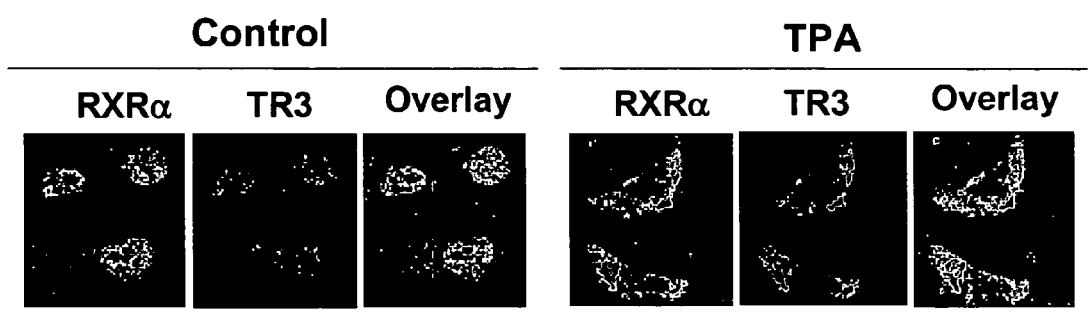
FIG. 2 illustrates the results of confocal microscopy analysis, showing co-localization of RXR and TR3 to the mitochondria in response to apoptotic stimuli.

In the absence of TPA, both TR3 and RXR.alpha. reside mainly in the nucleus. However, when cells are treated with TPA, TR3 and RXR.alpha. co-localize to the cytoplasm and their distribution patterns overlay extensively. (FIG. 2). To show that TR3 mitochondrial targeting requires RXR.alpha., Inventor used an siRNA technique to inhibit RXR.alpha. expression in LNCaP cells. siRNA techniques are well known in the art, and are described in Elbashir et al., 2001.

Figure 3:
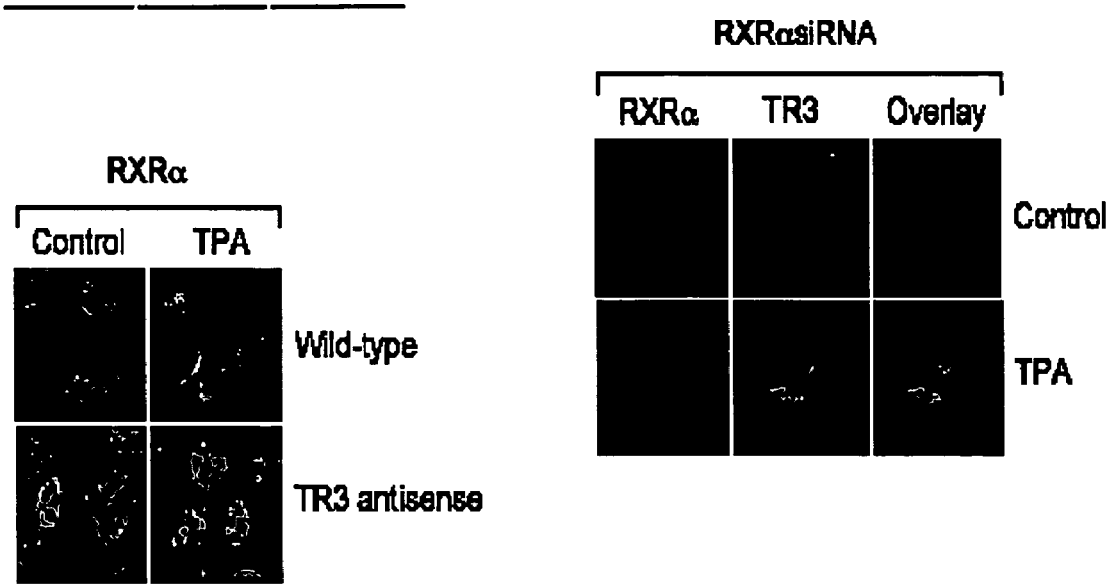
FIG. 3 illustrates the results of confocal microscopy analysis, showing that in response to apoptotic stimuli mitochondrial co-localization of RXR and TR3 is mutually dependent.

Transfection of LNCaP cells with RXR.alpha. siRNA is known to strongly reduce RXR.alpha. protein levels. The sub-cellular localization of TR3 in the presence and absence of an apoptosis inducing agent, such as TPA is then examined using well known techniques, preferably the immunostaining techniques described above. In contrast to that observed in wild-type LNCaP cells, cells transfected with RXR.alpha. siRNA showed TR3 was mainly confined in the nucleus despite TPA treatment. (FIG. 3).

Similarly, RXR.alpha. mitochondrial localization depends on TR3 expression. LNCaP cells stably expressing TR3 antisense RNA were treated with TPA, according to the technique described by Li et al, Science 289 1159-64, 2000. Expression of TR3 antisense RNA strongly inhibited TPA-induced TR3 expression in LNCaP cells. In contrast to that observed in wild-type LNCaP cells, RXR.alpha. was found only in the nucleus of the TR3 antisense stable clone, even though the cells were treated with TPA (FIG. 3). Thus, Inventor has discovered that in response to apoptotic stimuli the cytoplasmic localization of TR3 and RXR.alpha. are mutually dependant, and both the RXR and the TR3 overlay with mitochondrial associated proteins.

Nuclear Export Mechanism (NES).

Inventor has also discovered that the mechanism involved in RXR.alpha. and TR3 migration from the nucleus to the cytoplasm is via a CRM1-dependant nuclear export mechanism.

Figure 4:
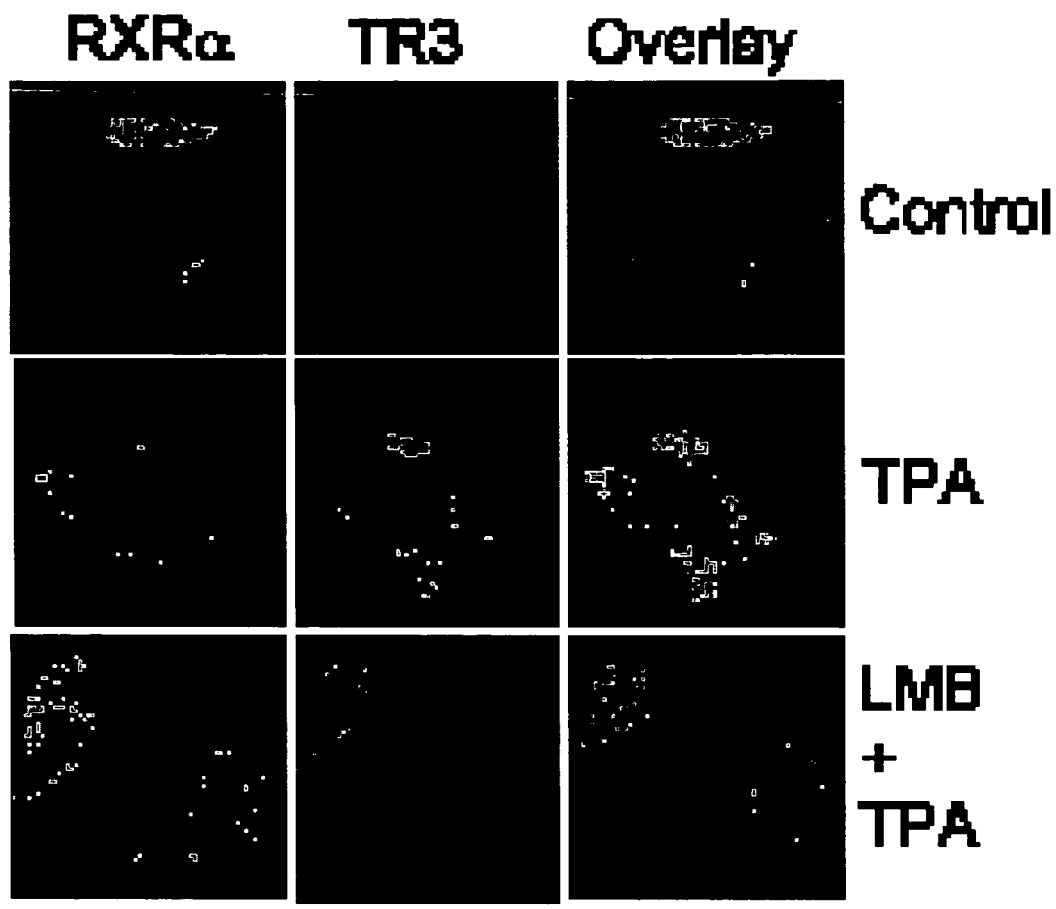
FIG. 4 illustrates the results of confocal microscopy analysis, showing co-localization of RXR and TR3 to the mitochondria in response to apoptotic stimuli mediated by a CRM1-dependent nuclear export.

Upon formation of the RXR.alpha./TR3 heterodimer, which is discussed below, CRM1-dependent nuclear export is mediated by a nuclear export sequence located near the C-terminus of RXR.alpha. A fusion protein created by combining GFP and amino acids 348-398 of RXR.alpha., is transfected into HEK293T cells. The transfected fusion protein is expressed in the HEK293T cells, and the fusion protein is isolated to the nucleus. Subsequently treating the HEK293T cells with TPA causes the fusion protein to export from the nucleus. Nuclear export of the fusion protein is inhibited by treating the cells with leptomycin-B (LMB), a specific inhibitor of CRM-1 dependant nuclear export. Thus, the RXR.alpha. and TR3 are exported out of the nucleus via the interaction of the nuclear export signal residing on RXR.alpha. and the CRM-1. (FIG. 4)

The RXR NES lies in Helix 7 of the RXR LBD. The amino acid sequence of RXR.alpha. is listed in SEQ ID No.: 1, and the nucleotide sequence encoding SEQ ID No.: 1 is listed in SEQ ID No.: 2. Furthermore, the amino acid sequence within SEQ ID No.: 1 that forms the nuclear export sequence (NES) is listed at SEQ ID No.: 3 and the corresponding nucleotide sequence is listed in SEQ ID No.: 4. Recent crystal structures of RXR.alpha. reveal that the Helix 7 undergoes dramatic conformational changes upon homodimerization, tetramerization, and heterodimerization with RAR and PPAR (Bourguet, W., et al. Mol Cell 5, 289-298 (2000); Gampe, R. T., et al. Mol Cell 5, 545-555 (2000a); Gampe, R. T., et al. Genes Dev 14, 2229-2241 (2000a)). The RXR.alpha. Helix 7 consists of an .alpha.-helix structure in its monomeric conformation (Bourguet, W., et al. Nature 375, 377-382 (1995)). However, it becomes a pi.-helix when RXR.alpha. homodimerizes, tetramerizes or heterodimerizes with PPAR-.gamma. or RAR, due to the presence of a glutamic acid residue (E352) in the middle of the Helix 7 (Bourguet, W., et al. Mol Cell 5, 289-298 (2000); Gampe, R. T., et al. Mol Cell 5, 545-555 (2000a); Gampe, R. T., et al. Genes Dev 14, 2229-2241 (2000a)). Thus, there is a transformation of helical geometry in the region where RXR.alpha. NES lies upon RXR.alpha. homodimerization, and heterodimerization silences the RXR.alpha. NES activity. Interestingly, and as discussed below, Inventor has discovered that RXR can form a heterodimer with TR3, which, depending on the cellular conditions, will have either an alpha. or a pi.-helix geometry. Such geometry accounts for the sub-cellular localization, and in turn the cellular function of said heterodimer.

Induction of RXR Cytoplasmic Localization by Prostaglandins.

Cyclopentenone prostaglandins (PGs) are naturally occurring eicosanoids that display varied biological activities, including antiviral and antitumoral effects. PGs are derived from fatty acids, primarily arachidonic acid, which are released from membrane phospholipids by the action of phospholipases. 15d-PGJ.sub.2 arises from the spontaneous dehydration of PGD.sub.2. 15d-PGJ.sub.2 plays a role in the regulation of inflammatory process, including inhibition of NF-kB activation. In addition, 15d-PGJ.sub.2 has potent antiproliferative activity and apoptosis inducing effect in a variety of tumor cell lines. The mechanism by which 15d-PGJ.sub.2 remains largely unknown. Recently, it was reported that 15d-PGJ.sub.2 binds and activates the peroxisome proliferator-activated receptor .gamma. (PPAR.gamma.) at micromolar concentration, suggesting that 15d-PGJ.sub.2 may act through PPAR.gamma. However, various studies have indicated that 15d-PGJ.sub.2 can act in a PPAR-.gamma.-independent mechanism. Recently, we reported that 15d-PGJ.sub.2 could effectively inhibit the expression of retinoic acid receptor beta (RAR.beta.) gene in various cancer cell lines.

Figure 6:
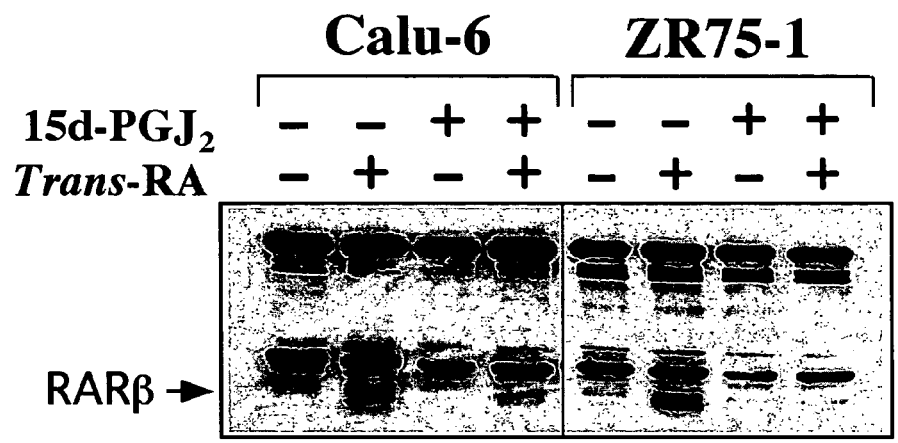
FIG. 6 is an immunoblot illustrating that treatment of Calu-6 lung cancer and ZR75-1 breast cancer cells potently inhibited the induction of RAR.beta. expression by trans-RA. The indicated cancer cells were treated for 24 h with or without trans-RA (10.sup.-6 M), or 15d-PGJ.sub.2 (5.micro.M) or their combination. RAR.beta. protein expression was determined by Western analysis.

The heterodimer of PPAR.gamma. and RXR binds to.beta.RARE in the RAR.beta. promoter, and the PPAR.gamma. ligand ciglitazone, strongly induces RAR.beta. expression when it is used together with RXR ligands. Interestingly, 15d-PGJ.sub.2 failed to induce RAR.beta. expression when it was used in combination with RXR ligands. FIG. 6 shows that treatment of Calu-6 lung cancer and ZR75-1 breast cancer cells potently inhibited the induction of RAR.beta. expression by trans-RA.

Figure 7:
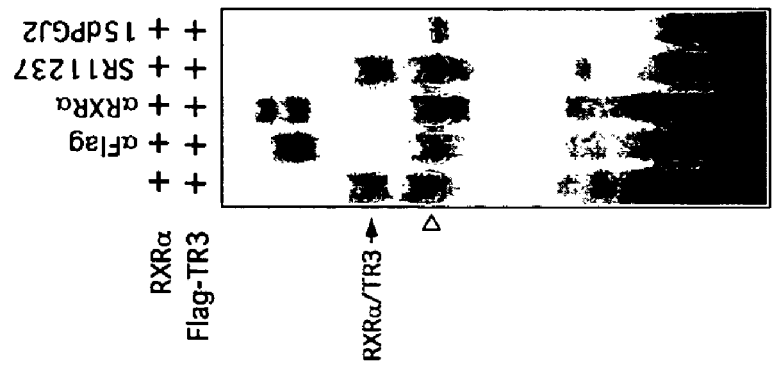
FIG. 7 is an immunoblot illustrating that incubation of the TR3/RXR.alpha. heterodimer with 15d-PGJ.sub.2 in vitro completely abolished the binding of the TR3/RXR.alpha. heterodimer to the .beta.RARE. In vitro translated RXR.alpha. and TR3 were incubated with 15d-PGJ.sub.2 (10.sup.-5 M) for 15 min in the absence or presence of anti-TR3 or anti-RXR.alpha. antibody. Following a further incubation with .sup.32P-radiolabelled .beta.RARE, the reactions were analyzed by EMSA.

Induction of RAR.beta. by retinoids is mainly mediated by the beta.RARE in the RAR.beta. promoter. The .beta.RARE can be activated by trans-RA through RAR/RXR heterodimer or TR3/RXR.alpha. heterodimer. It has been previously reported that binding of the .beta.RARE with the TR3/RXR.alpha. heterodimer contributes to the basal RAR.beta. expression. To study whether 15d-PGJ.sub.2 acted on the TR3/RXR.alpha. heterodimer to inhibit the heterodimer activity, Inventor investigated whether 15d-PGJ.sub.2 affected binding of the TR3/RXR.alpha. heterodimer to the beta.RARE by gel shift assay. The results (FIG. 7) demonstrate that incubation of the TR3/RXR.alpha. heterodimer with 15d-PGJ.sub.2 in vitro completely abolished the binding of the TR3/RXR.alpha. heterodimer to the .beta.RARE, demonstrating that 15d-PGJ.sub.2 can act on the TR3/RXR.alpha. heterodimer to regulate the .beta.RARE activity and the RAR.beta. expression.

Figure 8:
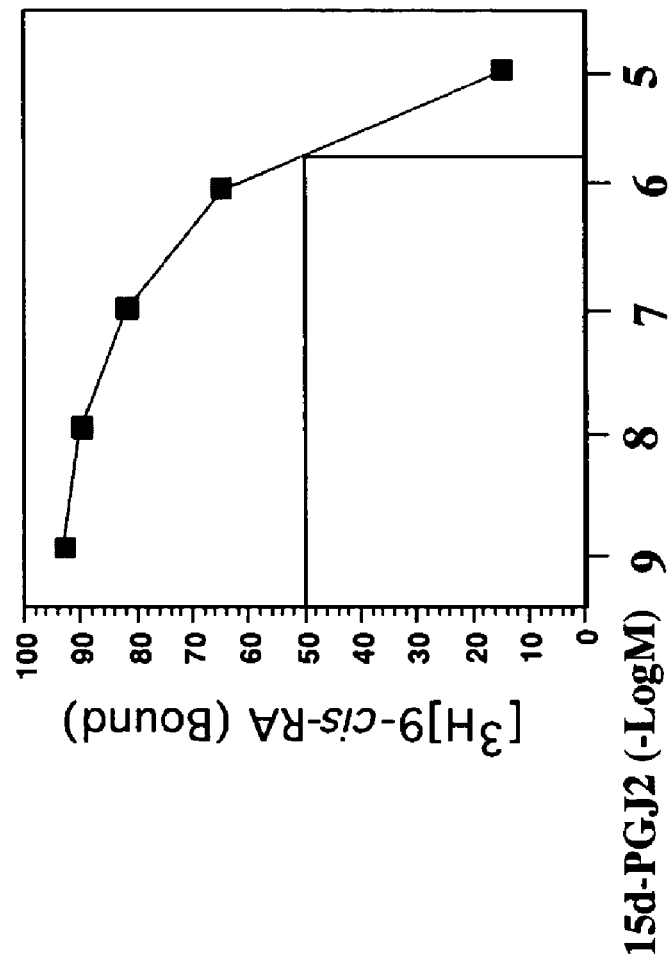
FIG. 8 is a dose response analysis illustrating that 15d-PGJ.sub.2 binds RXR.alpha. with high affinity conducted with 15d-PGJ.sub.2 in the competition binding assay. 15d-PGJ.sub.2 displaced [.sup.3H]9-cis-RA binding to the RXR ligand-binding domain with a Ki of 1.8.micro.M. The bacterially purified RXR.alpha. ligand-binding domain protein was incubated with 10 nM [.sup.3H]9-cis-RA in the presence or absence of the indicated concentration of 15d-PGJ.sub.2. After separation of bound from free radioactivity by elution through Sephadex G-25 desalting columns. Bound radioactivity eluted was quantitated by liquid scientillation counting.

The modulation of DNA binding of TR3/RXR heterodimer in vitro is unlikely due to its binding to TR3 because the recent crystal structures of TR3/NGFI-B indicates that TR3/NGFI-B contains no ligand binding pocket. Therefore, Inventor investigated the possibility that 15d-PGJ.sub.2 bound directly to RXR.alpha. This was assessed in a competition assay using [.sup.3H]9-cis-RA and the ligand-binding domain of RXR.alpha. expressed in $E$ $coli$. 15d-PGJ.sub.2 competed efficiently with [.sup.3H]9-cis-RA, indicating that it can directly interact with RXR.alpha. A dose response analysis (FIG. 8) was conducted with 15d-PGJ.sub.2 in the competition binding assay. 15d-PGJ.sub.2 displaced [.sup.3H]9-cis-RA binding to the RXR ligand-binding domain with a Ki of 1.8.micro.M. Thus, 15d-PGJ.sub.2 binds directly to RXR.alpha.

Figure 9:
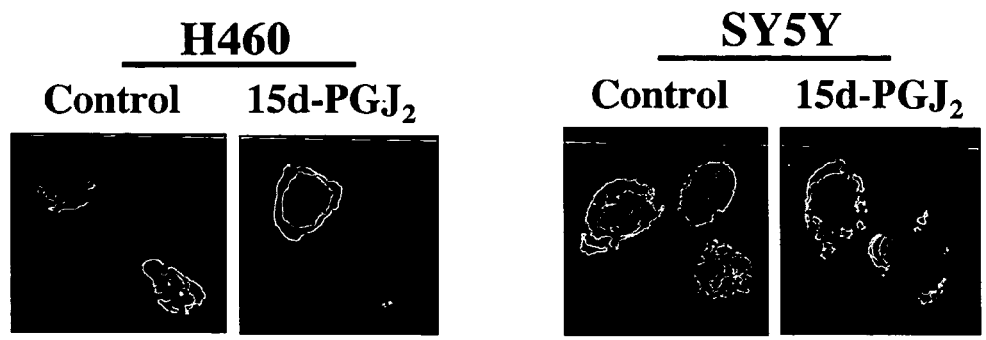
FIG. 9 is a series of confocal microscope images of immunostained cells illustrating that in the absence of 15d-PGJ.sub.2, RXR.alpha. transfected into H460 lung cancer or SY5Y neuroblastoma cells was confined in the nucleus. However, when cells were treated with 15d-PGJ.sub.2, significant amount of RXR.alpha. was found in the cytoplasm. Expression vector for Flag-RXR.alpha. was transfected into the indicated cell line. Cells were then treated with 15d-PGJ.sub.2 (5.micro.M) for 3 hr, then immunostained with anti-Flag antibody to detect RXR.alpha. Flag-RXR.alpha. was visualized by confocal microscopy.

The existence of a novel RXR pathway has been demonstrated that regulates nuclear export of TR3 and its mitochondrial targeting. Nuclear export of RXR or RXR/TR3 heterodimer is blocked by RXR ligand 9-cis-RA. To determine the role of 15d-PGJ.sub.2 binding on the new RXR pathway, a confocal microscopy analysis was performed to determine subcellular localization of RXR.alpha. in the presence or absence of 15d-PGJ.sub.2. In the absence of 15d-PGJ.sub.2, RXR.alpha. transfected into H460 lung cancer or SY5Y neuroblastoma cells was confined in the nucleus (FIG. 9). However, when cells were treated with 15d-PGJ.sub.2, significant amounts of RXR.alpha. was found in the cytoplasm.

Figure 10:
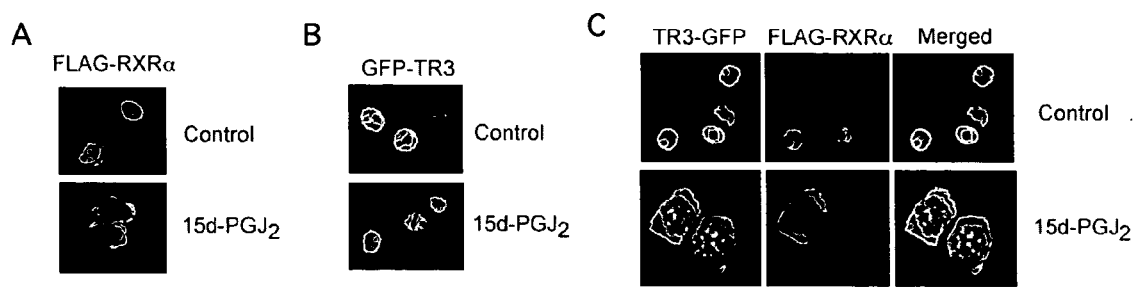
FIG. 10 is a series of confocal microscope images of immunostained PC12 cells illustrating that binding of 15d-PGJ.sub.2 to RXR.alpha. induces translocation of RXR.alpha. homodimer/monomer or TR3/RXR.alpha. heterodimer from the nucleus to the cytoplasm. Expression vectors for Flag-RXR.alpha. and GFP-TR3 were transfected into PC12 cells alone or together. Cells were then treated with 15d-PGJ.sub.2 (5.micro.M) for 3 hr, then immunostained with anti-Flag antibody to detect RXR.alpha. Flag-RXR.alpha. and GFP-TR3 were visualized by confocal microscopy, and their images merged.

Because RXR heterodimerizes with TR3, Inventor examined the effect of 15d-PGJ.sub.2 on TR3 subcellular localization in PC12 phaeochromocytoma cells. Similar to that observed in H460 and SY5Y cells, Flag-RXR.alpha. transfected into PC12 cells migrated from the nucleus to the cytoplasm when cells were treated with 15d-PGJ.sub.2 (FIG. 10). In contrast, GFP-TR3 expressed in PC12 cells did not. However, when both Flag-RXR.alpha. and GFP-TR3 were con-transfected, GFP-TR3 was found in the cytoplasm in cells treated with 15d-PGJ.sub.2. The distribution pattern of GFP-TR3 overlaid with that of Flag-RXR.alpha., suggesting that TR3 migrated as a TR3/RXR.alpha.heterodimer. These results demonstrated that binding of 15d-PGJ.sub.2 to RXR.alpha. induces translocation of RXR.alpha. homodimer/monomer or TR3/RXR.alpha. heterodimer from the nucleus to the cytoplasm.

RXR/TR3 Heterodimer.

Heterodimerization of RXR with other nuclear receptors, such as RAR, largely depends on a dimerization interface localized in RXR's ligand binding domain (LBD), and has been mapped to a region in the carboxyl-terminal (C-terminus) part of the receptor. Although RXR/TR3 heterodimerization has been studied, different interaction modalities have been described using different systems and approaches (Aarnisalo et al., 2002; Sacchetti et al., 2002; Wansa et al., 2002), suggesting that RXR and TR3 may interact differently under different conditions. Using a GST-pulldown assay, Inventor has discovered that these monomers form a unique heterodimer in response to apoptotic stimuli. The amino acid sequence of TR3 is listed at SEQ ID No.: 7, and the nucleotide sequence encoding SEQ ID No.: 7 is listed at SEQ ID No.: 8. A heterodimer is formed between SEQ ID No.: 1 and SEQ ID No.: 7 at their respective binding domains, SEQ ID No.: 5 and SEQ ID No.: 9. The nucleotide sequence coding SEQ ID No. 5 is listed at SEQ ID No.: 6. The nucleotide sequence coding SEQ ID No. 9 is listed at SEQ ID No.: 10.

Figure 5:
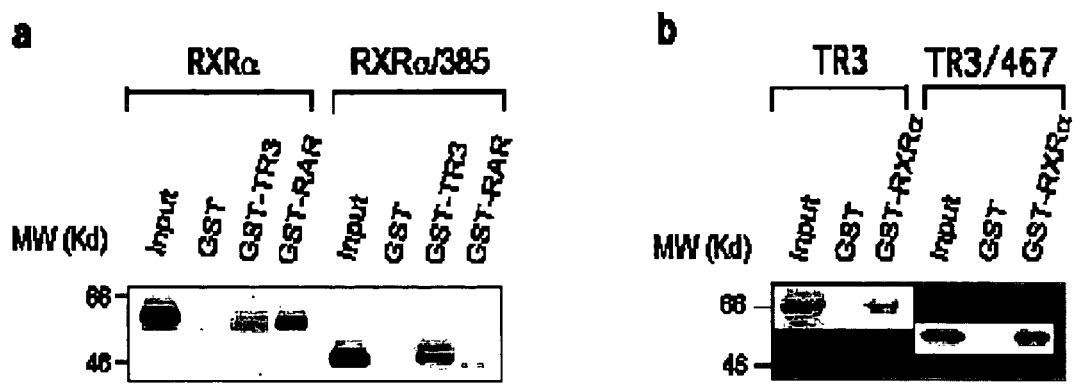
FIG. 5 is an immunoblot of a GST pull-down assay illustrating the interaction of RXR and TR3 in forming a heterodimer.

FIG. 5 shows that full-length RXR.alpha. is pulled down by GST-TR3. An RXR mutant comprising a truncated C-terminus (RXR.alpha./385) is also pulled down by GST-TR3, indicating that the C-terminal end of RXR.alpha. is not required for its interaction with TR3 in solution. Similarly, TR3/467, a TR3 mutant comprising a truncated C-terminus, was effectively pulled down by GST-RXR.alpha., indicating that the C-terminal end of TR3 was also dispensable for its interaction with RXR.alpha.

These results demonstrate that the C-terminal regions of RXR.alpha. and TR3 are not required for their interaction in solution, but instead, a dimerization interface located at the middle region of RXR.alpha. is required for its binding to TR3.

Inventor has further discovered that the unique heterodimer formation is regulated by RXR ligands. RXR ligand promotes RXR.alpha./TR3 heterodimer binding to the .beta.RARE. Thus, RXR ligand binding modulates RXR.alpha./TR3 interaction, resulting in a ligand bound heterodimer favorable for DNA binding and transactivation. The C-termini of TR3 and RXR.alpha. are required for their efficient binding and transactivation of the .beta.RARE, which is similar to other RXR heterodimers, such as RXR/RAR or RXR/TR (Zhang et al., 1992a). Thus, RXR ligands may induce formation of RXR.alpha./TR3 heterodimer through the common C-terminal dimerization domain. Such an RXR ligand induced dimerization switch may suppress the nuclear export of the RXR.alpha./TR3 heterodimer through its modulation of RXR.alpha./TR3 heterodimerization.

RXR.alpha./TR3 nuclear export is subject to regulation by apoptotic stimuli. RXR.alpha. and TR3 expressed endogenously are found mainly in the nucleus. However, Inventor has discovered that they resided at the mitochondria when cells were treated with apoptotic stimuli. Inventor has discovered that RXR.alpha./TR3 nuclear export is highly regulated by the switch of RXR.alpha./TR3 heterodimerization interfaces. In response to apoptotic stimuli an RXR.alpha./TR3 heterodimer is formed through their DNA Binding Domain ("DBD") dimerization interfaces. Thus, different RXR.alpha./TR3 heterodimers exist in a dynamic equilibrium depending on their cellular environment. Under normal conditions, both the DBD and C-terminal heterodimerization modalities participate in the formation of RXR.alpha./TR3 heterodimers, resulting in their localization in both the nucleus and cytoplasm. In response to apoptotic stimuli, RXR.alpha./TR3 heterodimers form preferentially through their DBD dimerization interfaces, leading to activation of the RXR.alpha. NES and the cytoplasmic localization of said heterodimer. In contrast, binding with rexinoids induces a switch of their heterodimerization interfaces, leading to silence of the RXR.alpha. NES and the nuclear localization of said heterodimer.

Inventor's discovery that RXR ligands regulate apoptosis through their effect on nuclear export of RXR.alpha. or RXR.alpha./TR3 heterodimer provides a novel approach for screening for and developing potent RXR-based apoptosis regulators. Additionally, Inventor's discovery that RXR and TR3 form a unique heterodimer provides a novel approach for screening for and developing potent RXR-based apoptosis regulators.

Effect of NSAID Sulindac Sulfide on RXR.alpha. Nuclear Export, RXR.alpha. Mitochondrial Targeting and Interaction with IkB Kinase Inventors have incubated cells in the presence and absence of sulindac sulfide (available from BIOMOL, Plymouth Meeting, Pa., as catalogue no.: AP-200-0005) and have determined the affect that this nonsteroidal antiinflammatory drug (NSAID) has on the subcellular localization of RXR.alpha., of the RXR.alpha./TR3 heterodimer and of RXR.alpha. and other cellular proteins known to play a role in apoptosis. Sulindac, and more precisely, the metabolite sulindac sulfide, induces apoptosis in cancer cells, and thus is a promising antineoplastic agent.

In vitro studies show that sulindac inhibits the growth of a variety of cancer cell types, including colon, breast, lung, prostate, pancreatic and hepatocellular cancer. In animals, sulindac inhibits chemically induced colon and mammary carcinogenesis as well as the growth of transplanted tumors in rodent models. Clinical trials show that sulindac prevents recurrence and reduced the number and size of adenomatous colorectal polyps in patients with familial adenomatous polyposis. Thus sulindac represents a useful antineoplastic agent for the chemoprevention and treatment of human cancer, and it is for this reason that Inventor's have selected this as one of many agents to screen for its effect on RXR.alpha localization using the techniques of the current discovery.

It is herein discovered and demonstrated that sulindac sulfide binds Retinoid X Receptor (RXR) alpha thereby mediating the apoptotic effects of sulindac sulfide in a variety of cancer cells. Furthermore, the binding of sulindac sulfide is shown to induce the translocation of RXR.alpha. from the nucleus to the cytoplasm, resulting in RXR.alpha. targeting the mitochondria or interacting with IkB kinases (IKK) to induce apoptosis.

Binding of Sulindac Sulfide with RXR.alpha.

Figure 12:
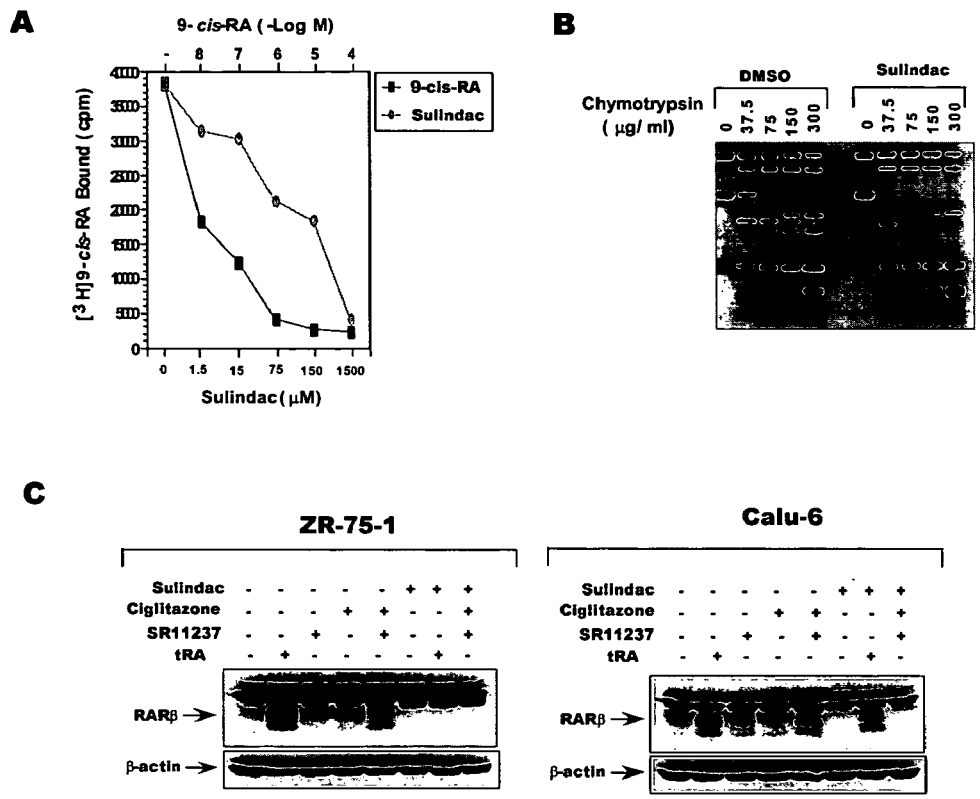
FIG. 12. NSAID sulindac sulfide binds RXR.alpha. to modulate its conformation and transactivation functions. (A) Competitive binding assay showing sulindac sulfide binds RXR.alpha. (B) Protein gel showing modulation of sensitivity of RXR.alpha. protein to chymotrypsin. (C) Western blot showing inhibition of RAR.beta. protein expression by sulindac sulfide in ZR-75-1 breast and Calu-6 lung cancer cells.

In order to demonstrate that sulindac sulfide binds RXR.alpha., a competitive binding assays was performed with [.sup.3H]9-cis-RA and the recombinant human RXR.alpha. LBD expressed in E. coli. As is shown in FIG. 12a, sulindac competes efficiently with [.sup.3H]9-cis-RA with an IC.sub.50 value of about 100.micro.M. (FIG. 12a). Briefly, to show that sulindac sulfide binds RXR.alpha., the RXR.alpha. ligand binding domain (SEQ ID No.: 11) was expressed in BL21 bacteria using the pET vector system available from Novagen (San Diego, Calif., catalogue no.: 69405, for example) and the purified RXR.alpha. LBD was then incubated with [.sup.3H]9-cis-RA (10.sup.-5 M) (Amersham Biosystems, Piscataway, N.J.) in the presence or absence of the indicated concentration of sulindac sulfide or unlabeled 9-cis-RA. The reactions were then eluted through a Sephadex G-25 column to separate the bound label from free label and the RXR.alpha. LBD-bound label was quantitated by liquid scintillation counting.

Isothermal titration calorimetry (ITC) confirmed the binding of sulindac sulfide to RXR.alpha (data not shown). ITC is a thermodynamic technique for monitoring the binding reaction of two components. When a protein binds a ligand, heat is either generated or absorbed, and quantitation of this heat allows very accurate determination of the binding dissociation constant (kD), reaction stoichiometry (n), enthalpy and entropy. Heat effects a small as 0.2.micro.cal can be measured and titrations can be done on as little as 1 ml of a dilute solution. (See generally, Pierce, M. M., Raman, C. S., and Nall, B. T., Methods, (1999) 19: 213-21)

The binding was also revealed by the effect of sulindac sulfide on sensitivity of RXR.alpha. protein to chymotrypsin digestion. (FIG. 12b). LBD protein was incubated in the absence (DMSO) or presence of sulindac sulfide (100.micro.M) and then subjected to digestion by chymotrypsin for 30 min. Briefly, SEQ ID No.: 11 was cloned into the pET vector system available from Novagen and the recombinant vector was transformed into and expressed in BL21 cells. Digested reactions were separated by SDS-PAGE and visualized by Commassie blue staining. $35.sup.S$ RXR protein was incubated for 30 minutes at room temperature in the presence or absence of 100.micro.M sulindac sulfide. Chymotrypsin was then added to a series of labeled protein reactions at final concentrations of 0, 37.5, 75, 150 and 300.micro.g per ml, and digestion proceeded for 20 minutes. The results are shown in FIG. 12b.

The effect of sulindac sulfide on RXR transactivation was investigated for its effect of RAR.beta. induction by all-trans-retinoic acid (tRA), which activates the RA response element (.beta.RARE) in the RAR.beta. promoter through an RAR/RXR heterodimer. Pre-treatment of both ZR-75-1 breast cancer cells (ATCC accession number CRL-1500) and Calu-6 lung cancer cells (ATCC accession number HTB-56) with sulindac sulfide effectively suppressed the inducing effect of tRA. (FIG. 12c). The .beta.RARE could be also activated by an RXR/PPAR heterodimer. The activation 6f RXR/PPAR heterodimer by the RXR ligand SR11237 and the PPAR-.gamma. ligand ciglitazone (Sigma, St. Louis, Mo., Cat no.: C-3974) was effectively inhibited by sulindac sulfide. Cells were treated for 24 hr with or without with trans-RA ($10.sup.-6$ M), or SR11237 ($10.sup.-6$ M), ciglitazone (10.micro.M), sulindac sulfide (100.micro.M) or the indicated combinations. RAR.beta. protein expression was determined by Western analysis. Together, these studies demonstrate that sulindac sulfide binds RXR.alpha. and inhibits its transactivation activity.

RXR.alpha. is Required for the Apoptotic Effect of Sulindac Sulfide

Figure 13:
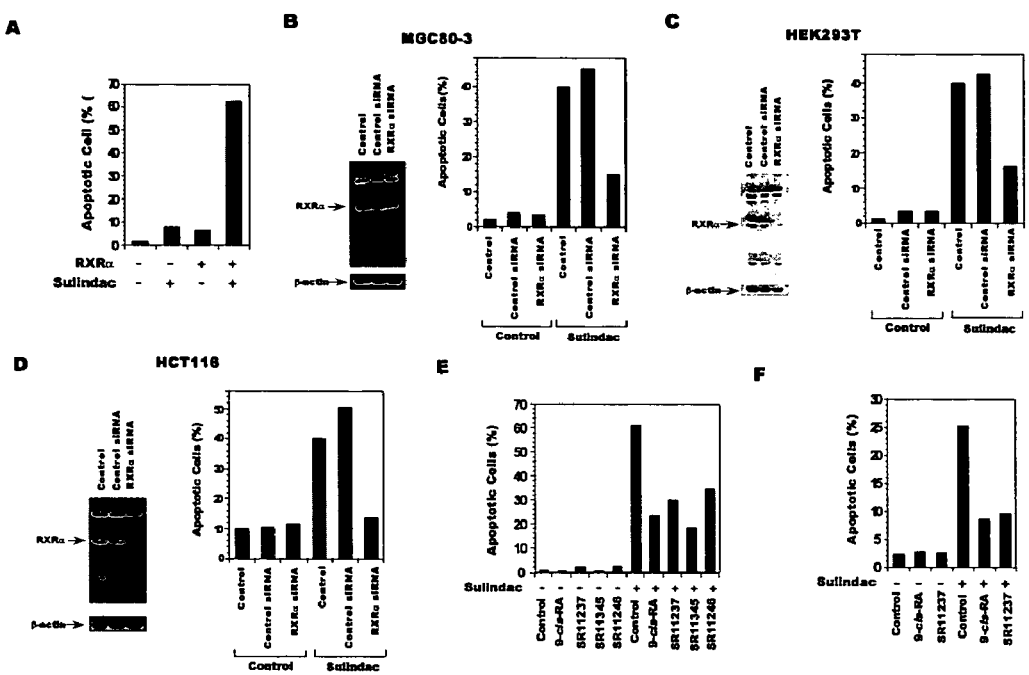
FIG. 13. Role of RXR.alpha. in apoptosis induction by sulindac sulfide. (A). Transfection of RXR.alpha. in CV-1 cells enhances the apoptotic effect of sulindac sulfide. (B through D). Inhibition of RXR.alpha. expression by RXR.alpha. siRNA suppresses the apoptotic effect of sulindac sulfide.

To determine the involvement of RXR.alpha. in sulindac sulfide-induced apoptosis of cancer cells, its effect on apoptosis of CV-1 cells (available from American Type Cell Culture, Manassas, Va., as accession number CCL-70) in the absence or presence of RXR.alpha. transfection was evaluated. FIG. 13a. RXR was cloned into a pGFP.C2 vector (GenBank Accession #: U19281) according to the procedure of Li et al., Science 289, 1159-1164 (2000). CV-1 cells were transfected with or without RXR.alpha. prior to treatment with sulindac sulfide (75.micro.M) for 24 hr. Apoptosis was determined by DAPI staining (4',6-Diamidino-2-phenylindole, available from Sigma Chemicals, St. Louis, Mo., as catalogue number D9542), and the presence of nuclear fragmentation and/or chromatin condensation is an indicator of apoptosis. In the absence of RXR.alpha., sulindac showed little inducing effect on apoptosis of CV-1 cells. However, when CV-1 cells were transfected with RXR.alpha., cells underwent extensive apoptosis in the presence of sulindac sulfide.

The requirement of RXR.alpha.was also examined using RXR.alpha. siRNA SEQ ID No.: 12 approach. MGC80-3 cells, HEK293T (ATCC, accession number CCL-1573) and HCT116 (ATCC, accession number CCL-247) cell lines were transfected with RXR.alpha. siRNA or control siRNA using oligofectamine (from Invitrogen, Corp). Cell samples from each cell line were lysed and the cell extracts were prepared by immunoblotting to determine RXR.alpha. expression. Cells transfected with RXR.alpha siRNA or control siRNA were treated with sulindac sulfide (75.micro.M) for 24 hr, and apoptosis was determined by DAPI staining. Transfection of RXR.alpha. siRNA into these several cell lines resulted in significant inhibition of RXR.alpha.expression revealed by Western blotting. (FIGS. 13b to 13d see the westemblot image on the left). When the apoptotic effect of sulindac sulfide on these cell lines was analyzed, we observed a significant reduction of apoptosis induced by sulindac sulfide in cells transfected with RXR.alpha. siRNA but not in cells transfected with control siRNA. (FIGS. 13b to 13d see the bar graph on the right). Thus, the inhibition of RXR.alpha. expression by RXR.alpha. siRNA suppresses the apoptotic effect of sulindac sulfide.

The involvement of RXRalpha. in modulating sulindac sulfide-induced apoptosis was also demonstrated by the inhibitory effect of several RXR.alpha. ligands, including 9-cis-RA, SR11237, SR11345, and SR11246, on sulindac sulfide-induced apoptosis. (FIGS. 13E-F). These results further show that RXR.alpha. plays a role in mediating the apoptotic effect of sulindac sulfide.

Sulindac Sulfide Induces RXR.alpha. Nuclear Export

Figure 14:
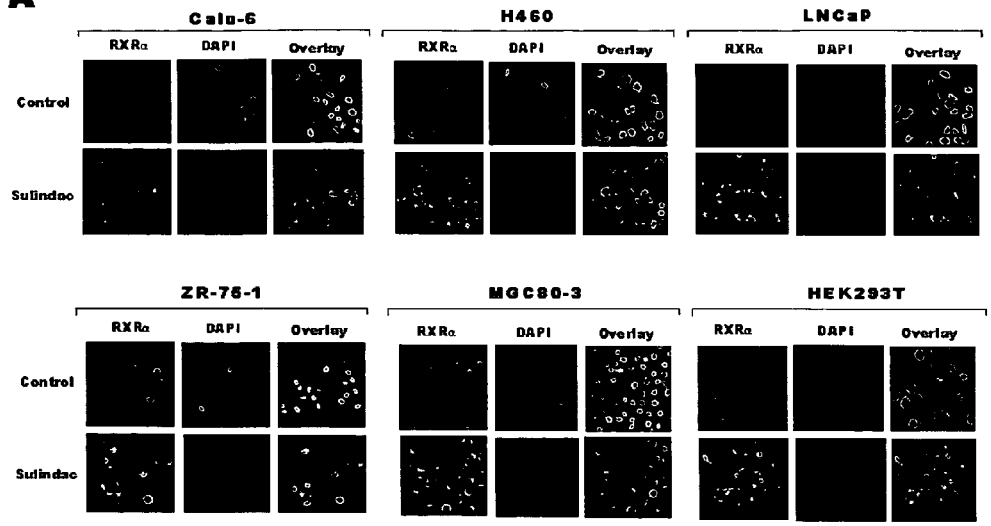
FIG. 14. Confocal microscopy showing that sulindac sulfide induces cytoplasmic localization of RXR.alpha. and RXR.alpha./TR3 heterodimer. (A). Induction of RXR.alpha. nuclear export. (B). Induction of TR3 nuclear export by sulindac is RXR.alpha. dependent.
Figure 14:
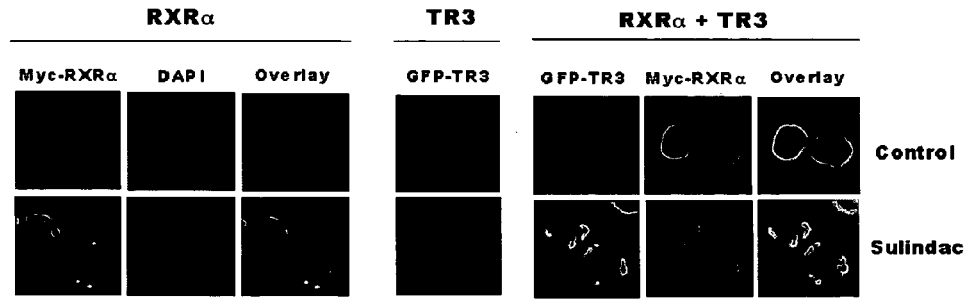

To determine the mechanism of RXR.alpha. mediated apoptosis in the presence of sulindac sulfide, Inventors examined the effect of sulindac sulfide on subcellular localization of RXR.alpha. As detailed above, RXR.alpha. mainly resides in the nucleus in several cancer cell lines investigated, including Calu-6, H460 lung cancer cells (ATCC accession number HTB-177) LNCaP prostate cancer (ATCC accession number CRL-1740), ZR-75-1 breast cancer, MGC80-3 stomach cancer and HEK293T cells. (FIG. 14a). Treatment of these cells with sulindac sulfide (75.micro.M) for 6 hr followed by immunostaining using a two stage detection system with an anti-RXR antibody (Santa Cruz Biotechnology, #D-20) first stage, thereby allowing visualization of the subcellular localization of RXR.alpha. Cells were also stained by DAPI to visualize nucleus. When these cells were treated with sulindac sulfide, RXR.alpha.was found mainly in the cytoplasm, demonstrating that sulindac sulfide induces translocation of RXR.alpha. from the nucleus to the cytoplasm. The effect of sulindac sulfide on RXR.alpha. subcellular localization was further illustrated by its effect on transfected RXR.alpha. in HEK293T cells. RXR.alpha. transfected into HEK293T cells resided in the nucleus. However, when cells were treated with sulindac sulfide, it was found in the cytoplasm.

The effect of sulindac sulfide is specific to RXR.alpha., as it does not affect the nuclear localization of TR3. Either TR3 alone, RXR.alpha. alone or TR3 and RXR.alpha. was transfected into HEK293T cells. Cells were then treated with sulindac sulfide (75.micro.M) for 6 hr. RXR.alpha and TR3 localization was determined by immunostaining, and cells were also stained by DAPI. RXR.alpha alone localizes to the cytoplasm in the presence of sulindac sulfide, while TR3 alone does not. When RXR.alpha. is co-transfected with TR3, both TR3 and RXR.alpha. are found in the cytoplasm following treatment with sulindac sulfide. Thus, the effect of sulindac sulfide on the cytoplasmic localization of TR3 depends on RXR.alpha. expression, probably due to their heterodimerization. Thus, sulindac sulfide induces nuclear export of RXR.alpha. and RXR.alpha./TR3 heterodimer. (FIG. 14b).

Sulindac Sulfide Induces Mitochondrial Targeting of RXRalpha.

Figure 15:
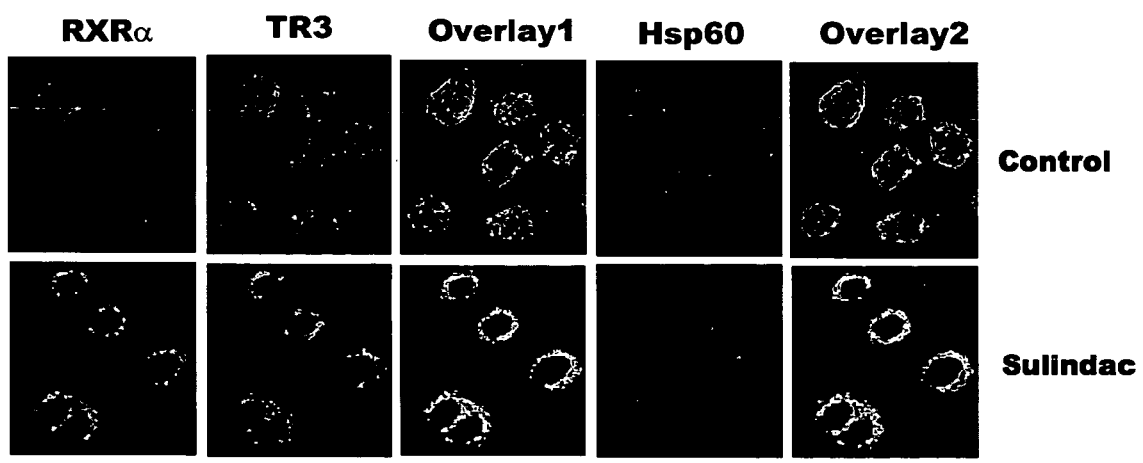
FIG. 15. Sulindac sulfide induces mitochondrial localization of RXR.alpha. and TR3, as shown by confocal microscopy.

The effect of sulindac sulfide on mitochondrial targeting of RXR.alpha. and TR3 was determined by treating H460 lung cancer cells with 75 micro.M sulindac sulfide for 6 hours and visualization of the cellular localization of these proteins by immunostaining. A two stage detection system was used having either anti-RXR or anti TR3 as a first stage (Santa Cruz Biotechnology and Abgent, respectively). In the absence of treatment, both RXR.alpha. and TR3 were found mainly in the nucleus. Treatment of cells with sulindac sulfide resulted in extensive co-localization of RXR.alpha. and TR3 with Hsp60, a mitochondria-specific protein, (FIG. 15), indicating that sulindac sulfide promotes RXR.alpha./TR3 mitochondrial targeting.

Figure 16:
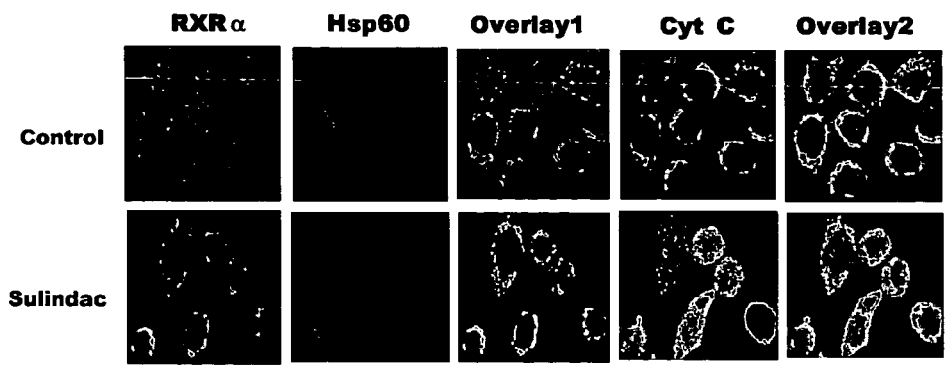
FIG. 16. Sulindac sulfide-induced RXR.alpha. mitochondrial localization is associated with cytochrome c release, shown by confocal microscopy.
Figure 16:
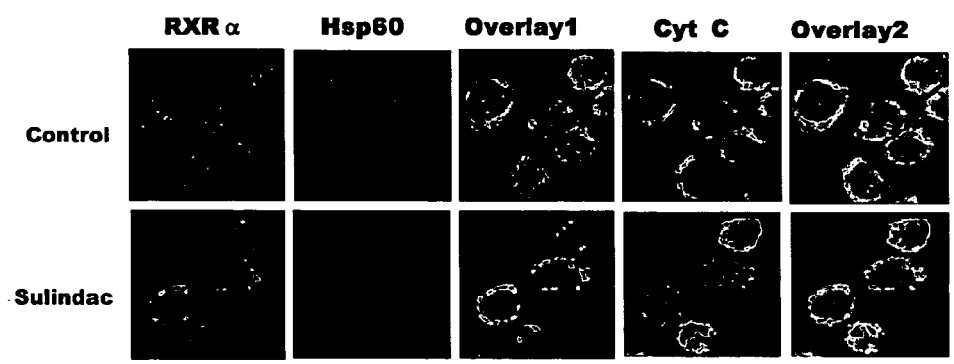
Figure 16:
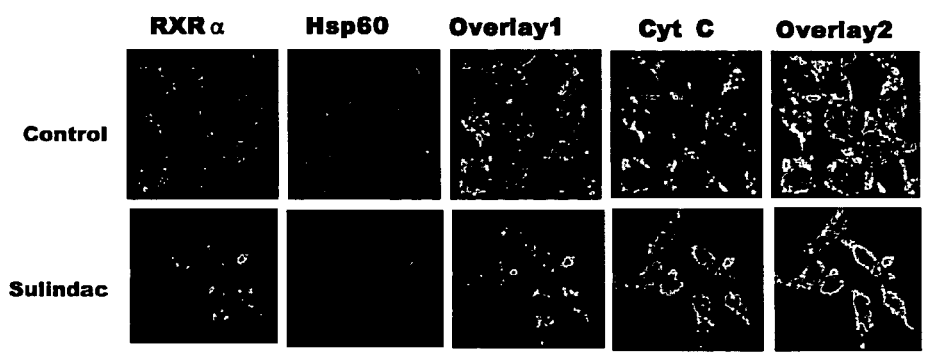

Sulindac Sulfide-Induced RXR.alpha. Mitochondrial Localization is Associated with Cytochrome C Release To uncover the consequence of RXR.alpha. mitochondrial localization induced by sulindac sulfide, H460, MGC80-3 and LnCap cells were treated with or without sulindac sulfide and RXR.alpha. mitochondrial and cytochrome c release were determined by immunostaining, as described above. Cells were treated with or without sulindac sulfide (75.micro.M) for 6 hr. Cells were then stained with RXR.alpha., Hsp6, and cytochrome c (cyt c). FIG. 16 shows that treatment of various cancer cell lines, including lung cancer H460 cells, stomach cancer MGC80-3 cells, and prostate cancer LNCaP cells, with sulindac sulfide results in RXR.alpha. mitochondrial localization. Furthermore, cytochrome c was massively released in sulindac sulfide treated cells. These results suggest that sulindac sulfide-induced RXR.alpha. mitochondrial targeting is responsible for cytochrome c release and apoptosis.

Sulindac Sulfide Promotes Interaction of RXRalpha. with IkB Kinases (IKK)

Figure 17:
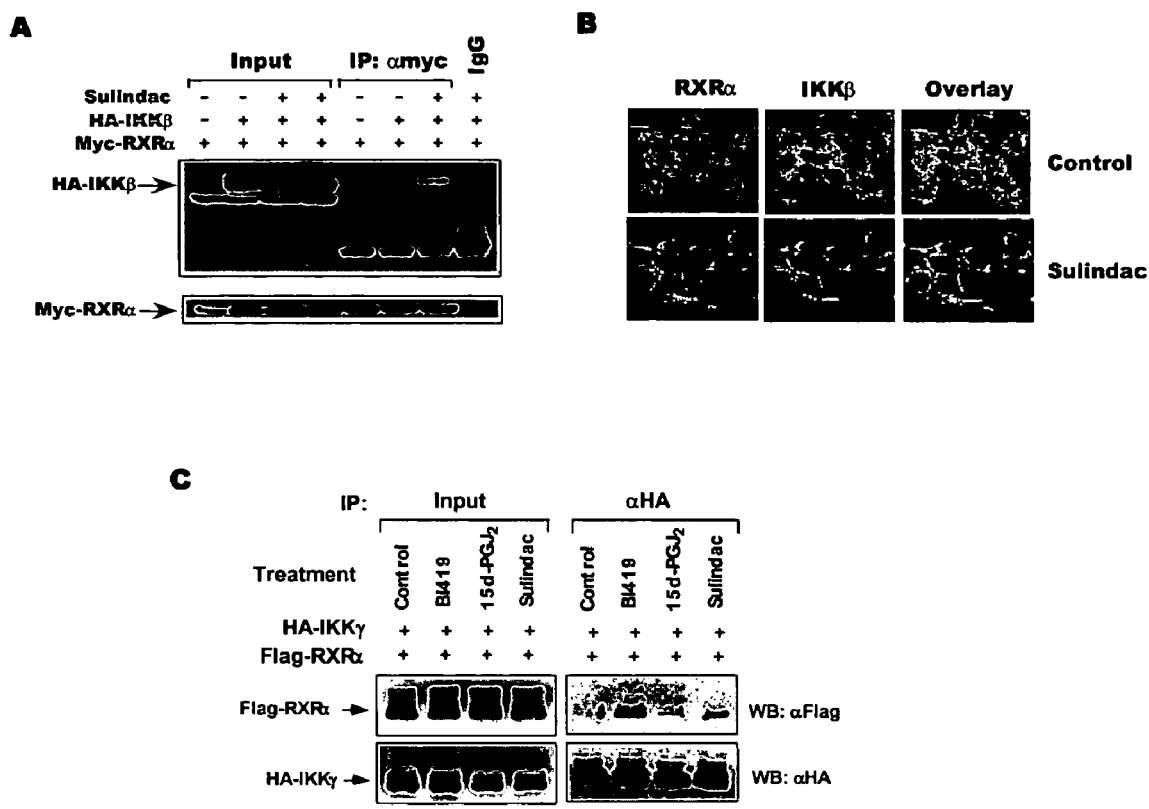
FIG. 17. RXR.alpha. interacts with IKK. (A) Interaction of RXR.alpha. with IKK.beta., as determined using tagged proteins and a two-stage antibody detection system. (B) Colocalization of RXR.alpha. and IKK.beta. as shown by confocal microscopy. (C) Interaction of RXR.alpha. with IKK.gamma., as determined using tagged proteins and a two-stage antibody detection system.

IKK is composed of three subunits: IKK.alpha. and IKK.beta., the catalytic subunits, and IKK.gamma., a regulatory subunit. IKK activation is required for NF-kB activation through its phosphorylation and degradation of IkB in response to proinflammatory stimuli. In addition, IKK also regulates cellular processes in a NF-kB-independent manner. We examined whether sulindac sulfide-induced cytoplasmic RXR.alpha. could interact with IKK. The indicated expression vector (pcDNA3 from Invitrogen, Corp) was transfected into HEK293T cells alone or together. After transfection, cells were treated with sulindac sulfide (75.micro.M) for 6 hr, and the interaction of RXR.alpha. and IKK.beta. was analyzed by co-immunoprecipitation assay. Co-immunoprecipitation assays showed an extensive interaction between RXR.alpha. and IKK.beta. when cells were treated with sulindac sulfide. (FIG. 17a). The interaction was also illustrated by their cytoplasmic co-localization in cells treated with sulindac sulfide. (FIG. 17b). RXR.alpha. also interacts with IKK.gamma., which was further promoted by sulindac sulfide and other compounds, including 15d-PGJ2 and B1419 that induce RXR.alpha. nuclear export. In this example, H460 cells were treated with or without sulindac sulfide (75.micro.M) for 6 hr, and cells were stained for RXR.alpha. and IKK.beta. (FIG. 17c). Together, these results demonstrate that cytoplasmic RXR.alpha. also exerts its biological effects through its interaction with IKK. HA-IKK.gamma. and Flag-RXR.alpha. expression vectors were transfected into HEK293T cells alone or together. After transfection, cells were treated with a new retinoid (BI419 (10.sup.-6 M), 15d-PGJ2 (5.micro.M), or sulindac sulfide (75.micro.M) for 6 hr. The interaction of RXR.alpha. and IKK.gamma. was studied by co-immunoprecipitation assay.

Thus, inventor has discovered that NSAID sulindac sulfide acts as a ligand of RXR.alpha. to induce its cytoplasmic localization, and that RXR.alpha. mediates the apoptotic effect of sulindac sulfide in a variety of cancer cells. It is further discovered that sulindac sulfide-induced cytoplasmic RXR.alpha. can either target mitochondria to induce cytochrome c release or interact with IKK to modulate NA-kB pathway.

Amino Acid and Nucleotide Sequences

Inventor has discovered amino acid and nucleotide sequences that are useful in the study of diseases and pathological conditions relating to RXR mediated apoptosis. These sequences include, but are not limited to: amino acid sequences that facilitate the cellular localization of RXR.alpha, with the proviso that the amino acid sequence is not SEQ ID No. 1 or SEQ ID No.: 7, but where the sequences can be domains of SEQ ID No.: 1 or SEQ ID No.: 7 and are substantially similar to an amino acid sequence selected from the group consisting of SEQ ID No.: 3, SEQ ID No.: 5 and SEQ ID No.: 9; and nucleotide sequences that encodes an amino acid sequence that facilitates the cellular localization of RXR.alpha, with the proviso that the nucleotide sequence is not SEQ ID No.: 2 or SEQ ID No. 8, but where the nucleotide sequences can be included within SEQ ID No.: 2 or SEQ ID No.: 8 and are substantially similar to a nucleotide sequence selected from the group consisting of SEQ ID No.: 4, SEQ ID No.: 6 and SEQ ID No.: 10.

EXAMPLES

Inventor's discovery that RXR can be induced to migrate from the nucleus of a cell to the cytoplasm wherein RXR may interact with cytoplasmic targets is useful for developing methods of screening for compounds that can modulate this migration. Inventor's discovery that a novel nongenotropic function of RXR can regulate apoptosis through mitochondrial targeting is useful for developing methods of screening for compounds that modulate apoptosis. Similarly, Inventor's discovery that RXR ligands can regulate apoptosis through their effect on RXR.alpha./TR3 heterodimer formation and on the nuclear export of RXR.alpha./TR3 heterodimer is useful for screening for compounds that modulate apoptosis. Test compounds found to modulate apoptosis are useful as pharmaceutical compositions for the treatment, prevention and otherwise for the regulation of pathological conditions, such as apoptosis.

The following non-limiting examples are useful in describing Inventor's discovery, and are in no way meant to limit the current invention. Those of ordinary skill in the art will readily adopt the underlying principles of Inventor's discovery to design a variety of screening assays without departing from the spirit of the current invention.

Example One

In a first screening method, cells are exposed to a variety of test compounds and are assayed for nuclear exportation of RXR.alpha.

LNCaP, (American Type Culture Collection, Cat. No. CRL-1740), or otherwise compatible cells, such as H460 lung cancer cells, SYSY neroblastoma cells, and COS-7 cells, are first seeded overnight in a tissue culture plate having 96 wells, 384 wells, 1536 wells or as many wells as are commercially available. For screening, two approaches can be taken. The first approach determines the effect of a compound on the migration of endogenous RXR.alpha. expressed in an appropriate cell-line. The second approach uses transfected RXR.alpha. with or without tags, such as GFP, Flag, or myc, in an appropriate cell line. Endogenous receptors are detected with an anti-RXR.alpha. antibody, while the detection of transfected receptors can be accomplished using either anti-RXR.alpha., or an antibody raised against the fused tag. Expression plasmids, such as GFP-RXR.alpha. fusion plasmid can be transfected into cells using standard procedures.

In the current example, GFP-fusion expression plasmids are prepared according to Li, H. et al., Science 298, 1159-64 (2000).

After 16-hours, cells were treated with one of the following: (1) 0.5%-Fetal Bovine Serum (FBS) only; (2) an apoptotic stimulus (i.e. TPA for LNCaP cells) in 0.5%-FBS; (3) Test compound in 0.5%-FBS. The TPA is added into the wells at a concentration of 100 ng/ml, while the test compounds are added in to the wells in various concentrations. The cells are incubated with the control or test compounds for 3 hours, then washed with 1 volume of a 10× Phosphate Buffered Saline (10×PBS) and fixed in a 4% paraformaldehyde solution.

Cells are then immunostained with appropriate antibody, and the sub-cellular localization of endogenous RXR.alpha. is visualized using MRC-1024 MP laser-scanning confocal microscope, (BioRad, Hercules Calif.). The images of receptor distribution in treated cells are compared to the sub-cellular localization of control cells. Whether RXR.alpha. migrates to the cytoplasm or mitochondria will be determined by immunostaining of a reference protein or an organelle. DAPI staining is used for detecting the nucleus, while mitochondria will be detected by immunostaining of Hsp60 and endoplasmic reticulum detected by staining with calreticulin.

Example Two

In a second screening method, cells are exposed to a variety of test compounds and are assayed for mitochondrial targeting by RXR.alpha./TR3 heterodimer.

LNCaP, (American Type Culture Collection, Cat. No. CRL-1740), or otherwise compatible cells, such as H460 lung cancer cells, SYSY neroblastoma cells, and COS-7 cells, are first seeded overnight in a tissue culture plate having 96 wells, 384 wells, 1536 wells or as many wells as are commercially available. For screening, two approaches can be taken. The first approach determines the effect of a compound on the migration of endogenous RXR.alpha. and TR3 expressed in an appropriate cell-line. The second approach uses transfected RXR.alpha. and TR3 with or without tags, such as GFP, Flag, or myc, in an appropriate cell-line. Endogenous receptors are detected with anti-RXR.alpha. and anti-TR3 antibodies, while the detection of transfected receptors can be accomplished using either anti-RXR.alpha., anti-TR3 or using an antibody raised against the fused tag. Expression plasmids, such as the Flag-RXR.alpha. fusion plasmid and the GFP-TR3 fusion plasmid can be transfected into cells using the standard procedure. In the current example, GFP-fusion expression plasmids are prepared according to Li, H. et al., Science 298, 1159-64 (2000).

After 16-hours, cells were treated with one of the following: (1) 0.5%-Fetal Bovine Serum (FBS) only; (2) an apoptotic stimulus (i.e. TPA for LNCaP cells) in 0.5%-FBS; (3) Test compound in 0.5%-FBS. The TPA is added into the wells at a concentration of 100 ng/ml, while the test compounds are added into the wells in various concentrations. The cells are incubated with the control or test compounds for 3 hours, then washed with 1 volume of 10× Phosphate Buffered Saline (10×PBS) and fixed in a 4% paraformaldehyde solution.

Cells are then immunostained and visualized as described in Example One, above. Whether RXR.alpha. and TR3 migrate to the cytoplasm or mitochondria will be determined by immunostaining of a reference protein or an organelle. DAPI staining is used for detecting the nucleus, while mitochondria will be detected by immunostaining of Hsp60 and endoplasmic reticulum is detected by staining of calreticulin.

Example Three

In a further screening method, cells are exposed to a variety of test compounds in the presence or absence of an inhibitor of RXR.alpha. and are then assayed for the effects on cell growth and apoptosis. Such inhibitors include, but are not limited to siRNA to inhibit RXR.alpha. or anti-sense TR3. In the current example, RXR.alpha. siRNA is used.

Cells are seeded in a tissue culture plate in media containing 0.5% FBS and transiently transfected with a GFP-RXR.alpha. construct as described in Example Two. Cells were then treated with one of the following: (1) 0.5%-FBS; (2) TPA; (3) TPA and RXR.alpha. siRNA in 0.5%-FBS; (4) Test compound; or (5) Test compound and RXR.alpha. siRNA. Cell growth and apoptosis will be determined by the MTT (3-(4,5-dimethylthiazol-2-yl)-2,5-diphenyl-tetrazolium bromide) assay and DAPI (4,6-diamidino-2-phenyl-lindole) assay. Lack of the growth inhibitory effect in cells transfected with RXR.alpha. siRNA as compared to untransfected cells indicates that RXR.alpha. is required for the growth inhibitory effect of a compound.

Example Four

In a further screening method, LMB is used to inhibit CRM1-dependant nuclear export of RXR.alpha. or the RXR.alpha./TR3 heterodimer. Thus, cells are exposed to a variety of test compounds in the presence or absence of LMB, and sub-cellular localization of RXR.alpha. or RXR.alpha./TR3 heterodimer amd growth inhibition and apoptosis of a compound are determined.

Cells are seeded in a tissue culture plate with or without transiently transfected RXR.alpha. and TR3 expression construct as described in Example One. Cells were then treated with one of the following: (1) 0.5%-FBS; (2) an apoptotic stimulus (i.e. TPA for LNCaP cells) in 0.5%-FBS; (3) an apoptotic stimulus (i.e. TPA for LNCaP cells) and LMB in 0.5%-FBS; (4) Test compound in 0.5%-FBS; or (5) Test compound and LMB in 0.5%-FBS.

Wells are stained and visualized according to Example One. The sub-cellular localization patters of the respective proteins are determined as in Example One. The growth inhibition and apoptosis determined as in Example Three.

In the absence of LMB, the cytoplasmic localization pattern indicates whether the test agent causes nuclear export of RXR.alpha. or RXR.alpha./TR3 heterodimer. For the test agents that show nuclear export of RXR.alpha. or RXR.alpha/TR3, the effect of LMB is assessed. If the addition of LMB causes a nuclear localization of RXR.alpha. or the RXR.alpha./TR3 heterodimer this showing indicates that the nuclear export is CRM1-dependant. Similarly, if wells containing the LMB display lack of growth inhibition and apoptosis, it indicates that the test compound acts to inhibit the growth and induce apoptosis of cells through its induction of cytoplasmic localization of RXR.alpha. or RXR.alpha./TR3 heterodimer.

Example Five

In a further screening method, RXR.alpha. and TR3 proteins synthesized in vitro or in bacteria are exposed to a variety of test compounds and are assayed for the formation of an RXR.alpha./TR3 heterodimer by the gel shift assay. Such an assay will determine which test compounds are capable of modulating the RXR.alpha./TR3 heterodimer formation.

RXR.alpha. and TR3 proteins are incubated in the absence or presence of a test compound. Following incubation, the mixture is incubated with $^{23}$P-labeled .beta.retinoic acid response element (.beta.RARE), and the binding of the RXR.alpha./TR3 heterodimer is analyzed by the gel-shift assay. 9-cis-RA, which enhances the binding of RXR/alpha/

TR3 heterodimer to DNA, is used as a positive control, whereas 15d-PGJ.sub.2, which abolishes the heterodimer binding, is used as a negative control. The enhancement of the heterodimer binding by a compound will indicate that the compound retains the RXR.alpha./TR3 heterodimer in the nucleus and likely induces transcriptional activity of the heterodimer through its induction of RXR.alpha./TR3 heterodimerization at their LBD dimerization interfaces. Similarly, inhibition of the heterodimer binding by a compound likely indicates that the compound induces nuclear export of the heterodimer through its induction of RXR.alpha./TR3 heterodimerization at their DBD dimerization interfaces.

Example Six

In a further screening method, the cells are exposed to a variety of test compounds and are assayed for mitochondrial targeting. In this example, cells are exposed to test compounds in the presence and absence of anti-RXR-NES antibodies. Such an assay will determine whether those compounds that facilitate apoptosis are doing so via the RXR.alpha./TR3 heterodimer pathway.

LNCaP cells, or other compatible cell lines are seeded in a tissue culture plate having 96 wells, 384 wells, 1536 wells or as many wells as are commercially available. Cells are then treated with one of the following reactions mixtures: (1) test compound in 0.5% FBS; or (2) test compound and anti-RXR-NES antibody. Additionally, control wells containing FBS alone, FBS and a known apoptosis inducing agent such as TPA, FBS and anti-RXR-NES antibody, or FBS, anti-RXR-NES antibody and TPA. The reaction mixtures are then incubated, washed with PBS and fixed in paraformaldehyde, as described above.

Wells are stained for mitochondria associated protein Hsp60 using anti-Hsp60 goat IgG followed by Cy3 conjugated anti-goat IgG (Pharmingen, San Diego, Calif.). Wells are also stained for RXR or RXR/TR3 using a similar two-stage antibody technique. Fluorescent images were collected and analyzed using MRC-1024 MP laser-scanning confocal microscope, and the images were overlayed.

The sub-cellular localization of the heterodimer is compared to the sub-cellular localization of Hsp60. In wells containing test compounds only the overlay of either RXR.alpha. or RXR.alpha./TR3 with that of the Hsp60 indicates that the test compound activates or enhances RXR.alpha. mediated apoptotic regulation. In wells containing test compound and anti-RXR-NES, the localization of the RXR.alpha. or RXR.alpha./TR3 in the nucleus indicated that the apoptotic stimuli action of a test compound is inhibited by preventing NES mediated migration of the heterodimer.

Example Seven

In a further screening method, fluorescence resonance energy transfer (FRET) will be used for high throughput screen for compounds that induce migration of RXR.alpha. and RXR.alpha./TR3 heterodimer from the nucleus to plasma membrane and various intracellular organelles, such as mitochondria, golgi, and endoplasmic reticulum (ER). FRET techniques are well known in the art. (See e.g., Selvin PR. Fluorescence resonance energy transfer, Methods Enzymol 246, 300-334 (1995); Sambrook, J., et al. Molecular Cloning: A Laboratory Manual, (2001). To study whether the receptors migrate to the plasma membrane, a plasma membrane targeting sequence, such as a CAAX box containing the COOH-terminus of K-ras is fused to blue fluorescence protein (BFP) or other appropriate fluorescence proteins, which are known in the art. To study mitochondrial targeting, a mitochondrial targeting sequence, such as the trans-membrane domain of the yeast outer mitochondrial membrane protein Mas70p, will be fused to BFP or appropriate fluorescence protein. To study ER targeting, an ER-specific targeting sequence, such as the ER-targeting sequence from the ER-specific isoforms of cytochrome b5, will be fused to BFP or appropriate fluorescence protein. To study golgi targeting, a golgi-specific targeting sequence from ST3Gal-transferase I will be fused to BFP or appropriate fluorescence protein. The fusion plasmids and GFP-RXR.alpha. or GFP-TR3 will be stably transfected into COS-7 cells or other compatible cells. Stable clones expressing GFP-RXR.alpha. or GFP-TR3 and one of the BFP-Targeting Sequence fusions will be used in a high throughput screening of compounds that induce targeting of RXR.alpha. or TR3 to plasma membrane or other intracellular organelles by FRET technology described.

Treatment Methods

Inventors have discovered novel methods for the treatment of diseases and pathological conditions by modulating RXR mediated apoptosis of a cell comprising administering to a patient an agent that is capable of modulating RXR mediated apoptosis, wherein said agent is administered in a sufficient quantity. In one embodiment, the agents modulate RXR mediated apoptosis of a cell by affecting the sub-cellular migration of RXR from the nucleus of a cell to a non-nuclear cell target. In a preferred embodiment, the agents modulate RXR mediated apoptosis by affecting the conformation of RXR. More preferably the agents modulate RXR mediated apoptosis by affecting the conformation of RXR/TR3 heterodimer. In another embodiment, the agents modulating RXR mediated apoptosis are selected from the group consisting of a peptide, polypeptide, peptidomimetic, an antibody or antibody fragment, siRNA, anti-sense RNA, gene therapy products and a nucleotide sequence. Preferably the agent is an exogenous nucleotide sequence administered in a quantity sufficient to modulate RXR mediated apoptosis. Exogenous nucleotide sequences can be administered to a patient using an administration system selected from the group consisting of a nucleic acid vector system, microinjection, a gene gun and a liposome. Useful nucleotide sequences include, but are not limited to RNA molecules that have a sequence that is antisense to a portion of the native RXR RNA transcript; DNA sequences substantially identical to the nucleotide sequence selected from the group consisting of SEQ ID No 2, SEQ ID No.: 4, SEQ ID No.: 6, SEQ ID No.: 8 and SEQ ID No.: 10; DNA sequences that encode a polypeptide having a sequence substantially identical to the amino acid sequence selected from the group consisting of SEQ ID No 1, SEQ ID No.: 3, SEQ ID No.: 5, SEQ ID No.: 7 and SEQ ID No.: 9. In an further preferred embodiment the agent is an eicosanoid, more preferably a prostaglandin and most preferably 15-Deoxy-.delta.sup. 12,14-prostaglandin J.sub.2 (15d-PGJ-.sub.2). Alternatively, the agent is a non-steroidal anti-inflammatory drug selected from the group consisting of indomethacin, diclofenac and sulindac.

Pharmaceutical Compositions

Methods of using the compounds and pharmaceutical compositions of the invention are also provided herein. The methods involve both in vitro and in vivo uses of the compounds and pharmaceutical compositions for altering preferred nuclear receptor activity, in a cell type specific fashion.

In certain embodiments, the claimed methods involve the discovery and use of apoptosis modulating compounds.

Once identified as a modulator using a method of the current invention, an agent can be put in a pharmaceutically acceptable formulation, such as those described in Remington's Pharmaceutical Sciences, 18th ed., Mack Publishing Co., Easton, Pa. (1990), incorporated by reference herein, to generate a pharmaceutical composition useful for specific treatment of diseases and pathological conditions.

Agents identified by the methods taught herein can be administered to a patient either by themselves, or in pharmaceutical compositions where it is mixed with suitable carriers or excipient(s). In treating a patient exhibiting a disorder of interest, a therapeutically effective amount of agent or agents such as these is administered. A therapeutically effective dose refers to that amount of the agent resulting in amelioration of symptoms or a prolongation of survival in a patient.

The agents also can be prepared as pharmaceutically acceptable salts. Examples of pharmaceutically acceptable salts include, but are not limited to acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the agent is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the agent, for example, to increase the solubility of the agent. Examples of carriers and excipients include calcium carbonate, calcium phosphate, various sugars or types of starch, cellulose derivatives, gelatin, vegetable oils, polyethylene glycols and physiologically compatible solvents.

Toxicity and therapeutic efficacy of such agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_5O/ED_{50}$. Agents which exhibit large therapeutic indices are preferred. The data obtained from these cell culture assays and animal studies can be used in formulating a range of dosage for use in humans. The dosage of such agents lies preferably within a range of circulating concentrations that include the $ED_{50}$ with little or no toxicity. The dosage may vary within this range depending upon the dosage form employed and the route of administration utilized.

For any agent identified by the methods taught herein, the therapeutically effective dose can be estimated initially from cell culture assays. For example, a dose can be formulated in animal models to achieve a circulating plasma concentration range that includes the $IC_{50}$ as determined in cell culture (i.e., the concentration of the test agent which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, Ch. 1 p. 1 (1975)). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the agents herein disclosed into dosages suitable for systemic administration is contemplated. With proper choice of carrier and suitable manufacturing practice, these agents, in particular, those formulated as solutions, may be administered parenterally, such as by intravenous injection. The agents can be formulated readily using pharmaceutically acceptable carriers well known in the art into dosages suitable for oral administration. Such carriers enable the agents of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the context of the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active agents into preparations which can be used pharmaceutically. The preparations formulated for oral administration may be in the form of tablets, dragees, capsules, or solutions. The pharmaceutical compositions contemplated by the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active agents in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the agents to allow for the preparation of highly concentrated solutions.

Pharmaceutical preparations for oral use can be obtained by combining the active agents with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added.

Some methods of delivery that may be used include:
a. encapsulation in liposomes,
b. transduction by retroviral vectors,
c. localization to nuclear compartment utilizing nuclear targeting site found on most nuclear proteins,
d. transfection of cells ex vivo with subsequent reimplantation or administration of the transfected cells,
e. a DNA transporter system.

What is claimed is:

1. A method for screening agents that induce apoptosis, comprising:
   (a) providing a cell containing Retinoid X Receptor (RXR) and TR3 located in the nucleus of said cell;
   (b) incubating said cell with a test agent, wherein the test agent is an RXR ligand;
   (c) assessing the ability of the RXR ligand to induce migration of a heterodimer formed by RXR and TR3 from the nucleus to a non-nuclear cell target selected from the group consisting of cell cytoplasm, endoplasmic reticulum, golgi, mitochondria and plasma membrane; and
   (d) identifying those RXR ligands capable of inducing migration of RXR-TR3 heterodimer from the nucleus to the non-nuclear cell target as apoptosis inducing agents.

2. The method of claim 1 wherein the RXR ligand is an eicosanoid.

3. The method of claim 2 wherein the eicosanoid is a prostaglandin.

4. The method of claim 1 wherein the RXR ligand is a non-steroidal anti-inflammatory drug.

5. The method of claim 1 wherein the cell is a mammalian cell.

6. The method of claim 5, wherein the mammalian cell is a human cancer cell.

7. The method of claim 1, wherein the ability of the test agent RXR ligand to induce migration of RXR-TR3 heterodimer from the nucleus to the non-nuclear cell target is assessed by detecting the co-localization of RXR and TR3.

8. The method of claim 7, wherein the co-localization of RXR and TR3 is detected by fluorescence microscopy.

9. The method of claim 1, wherein the non-nuclear cell target is cell cytoplasm.

10. The method of claim 1, wherein the non-nuclear cell target is the endoplasmic reticulum.

11. The method of claim 1, wherein the non-nuclear cell target is the golgi.

12. The method of claim 1, wherein the non-nuclear cell target is mitochondria.

13. The method of claim 1, wherein the non-nuclear cell target is the plasma membrane.

14. The method of claim 1, wherein the test agent RXR ligand changes conformation of the RXR-TR3 heterodimer by switching a heterodimerization interface, thereby inducing migration of the RXR-TR3 heterodimer from the nucleus to the non-nuclear target.

15. The method of claim 1, wherein the test agent RXR ligand is a small organic molecule.

16. A method for screening agents that induce apoptosis, comprising:

(a) providing a cell containing Retinoid X Receptor (RXR) and TR3 located in the nucleus of said cell;

(b) incubating said cell with an RXR ligand, wherein the RXR ligand is a small organic molecule;

(c) assessing the ability of the RXR ligand to induce migration of a heterodimer formed by RXR and TR3 from the nucleus to a non-nuclear cell target, wherein the RXR ligand changes conformation of the RXR-TR3 heterodimer by switching a heterodimerization interface, thereby inducing migration of the RXR-TR3 heterodimer from the nucleus to the non-nuclear target; and (d) identifying those RXR ligands capable of inducing migration of the RXR-TR3 heterodimer from the nucleus to the non-nuclear cell target as apoptosis inducing agents.

17. The method of claim 16, wherein the RXR ligand is an eicosanoid or a prostaglandin.

18. The method of claim 17, wherein the non-nuclear cell target is a cell cytoplasm, endoplasmic reticulum, golgi, mitochondria or plasma membrane.

19. The method of claim 16, wherein the RXR ligand is a non-steroidal anti-inflammatory drug.

20. The method of claim 16, wherein the cell is a human cancer cell.

* * * * *

```
                          SEQUENCE LISTING

<160> NUMBER OF SEQ ID NOS: 12

<210> SEQ ID NO 1
<211> LENGTH: 462
<212> TYPE: PRT
<213> ORGANISM: Human

<400> SEQUENCE: 1

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
            85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140
```

```
Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
        355                 360                 365

Cys Leu Arg Ala Ile Val Leu Phe Asn Pro Asp Ser Lys Gly Leu Ser
    370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430

Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
    450                 455                 460

<210> SEQ ID NO 2
<211> LENGTH: 1389
<212> TYPE: DNA
<213> ORGANISM: Human

<400> SEQUENCE: 2
atggacacca aacatttcct gccgctcgat ttctccaccc aggtgaactc ctccctcacc    60
tccccgacgg ggcgaggctc catggctgcc ccctcgctgc accgtccct ggggcctggc    120 atcggctccc cggacagct gcattctccc atcagcaccc tgagctcccc catcaacggc    180
atgggcccgc ctttctcggt catcagctcc ccatgggcc ccactccat gtcggtgccc    240 accacaccca ccctgggctt cagcactggc agccccagc tcagctcacc tatgaacccc    300
gtcagcagca gcgaggacat caagcccccc ctgggcctca atggcgtcct caaggtcccc    360
```

```
gcccacccct caggaaacat ggcttccttc accaagcaca tctgcgccat ctgcggggac    420
cgctcctcag gcaagcacta tggagtgtac agctgcgagg ggtgcaaggg cttcttcaag    480
cggacggtgc gcaaggacct gacctacacc tgccgcgaca caaggactg cctgattgac     540 aagcggcagc ggaaccggtg ccagtactgc cgctaccaga agtgcctggc catgggcatg    600
aagcgggaag ccgtgcagga ggagcggcag cgtggcaagg accggaacga gaatgaggtg    660
gagtcgacca gcagcgccaa cgaggacatg ccggtggaga ggatcctgga ggctgagctg    720
gccgtggagc ccaagaccga gacctacgtg gaggcaaaca tggggctgaa ccccagctcg    780
ccgaacgacc ctgtcaccaa catttgccaa gcagccgaca aacagctttt caccctggtg    840
gagtgggcca gcggatcccc acacttctca gagctgcccc tggacgacca ggtcatcctg    900
ctgcgggcag gctggaatga gctgctcatc gcctccttct cccaccgctc catcgccgtg    960
aaggacggga tcctcctggc caccgggctg cacgtccacc ggaacagcgc ccacagcgca   1020
ggggtgggcg ccatctttga cagggtgctg acggagcttg tgtccaagat gcgggacatg   1080
cagatggaca agacggagct gggctgcctg cgcgccatcg tcctctttaa ccctgactcc   1140
aaggggctct cgaaccccgg ccgaggtgga ggcgctgaggg agaaggtcta tgcgtccttg   1200
gaggcctact gcaagcacaa gtacccagag cagccgggaa ggttcgctaa gctcttgctc   1260
cgcctgccgg ctctgcgctc catcgggctc aaatgcctgg aacatctctt cttcttcaag   1320
ctcatcgggg acacacccat tgacaccttc cttatggaga tgctggaggc gccgcaccaa   1380
atgacttag                                                          1389

<210> SEQ ID NO 3
<211> LENGTH: 21
<212> TYPE: PRT
<213> ORGANISM: Human

<400> SEQUENCE: 3

Arg Val Leu Thr Glu Leu Val Ser Lys Met Arg Asp Met Gln Met Asp
1               5                   10                  15

Lys Thr Glu Leu Gly
            20

<210> SEQ ID NO 4
<211> LENGTH: 63
<212> TYPE: DNA
<213> ORGANISM: Human

<400> SEQUENCE: 4
agggtgctga cggagcttgt gtccaagatg cgggacatgc agatggacaa gacggagctg    60
ggc                                                                 63

<210> SEQ ID NO 5
<211> LENGTH: 19
<212> TYPE: PRT
<213> ORGANISM: Human

<400> SEQUENCE: 5

Arg Gln Arg Asn Arg Cys Gln Tyr Cys Arg Tyr Gln Lys Cys Leu Ala
1               5                   10                  15

Met Gly Met

<210> SEQ ID NO 6
<211> LENGTH: 57
<212> TYPE: DNA
```

<213> ORGANISM: Human

<400> SEQUENCE: 6
cggcagcgga accggtgcca gtactgccgc taccagaagt gcctggccat gggcatg        57

<210> SEQ ID NO 7
<211> LENGTH: 598
<212> TYPE: PRT
<213> ORGANISM: Human

<400> SEQUENCE: 7

```
Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
            20                  25                  30

Pro Thr Met Asp Leu Ala Ser Pro Glu Ala Ala Pro Ala Ala Pro Thr
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
            100                 105                 110

Pro Gly Pro Leu Ser Gly Pro Val Asp Glu Ala Leu Ser Ser Ser Gly
        115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270

Asn Ala Ser Cys Gln His Tyr Gly Val Arg Thr Cys Glu Gly Cys Lys
        275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350
```

-continued

```
            Pro Lys Gln Pro Pro Asp Ala Ser Pro Ala Asn Leu Leu Thr Ser Leu
                355                 360                 365

Val Arg Ala His Leu Asp Ser Gly Pro Ser Thr Ala Lys Leu Asp Tyr
                370                 375                 380

Ser Lys Phe Gln Glu Leu Val Leu Pro His Phe Gly Lys Glu Asp Ala
            385                 390                 395                 400

Gly Asp Val Gln Gln Phe Tyr Asp Leu Leu Ser Gly Ser Leu Glu Val
                            405                 410                 415

Ile Arg Lys Trp Ala Glu Lys Ile Pro Gly Phe Ala Glu Leu Ser Pro
                        420                 425                 430

Ala Asp Gln Asp Leu Leu Leu Glu Ser Ala Phe Leu Glu Leu Phe Ile
                    435                 440                 445

Leu Arg Leu Ala Tyr Arg Ser Lys Pro Gly Glu Gly Lys Leu Ile Phe
                450                 455                 460

Cys Ser Gly Leu Val Leu His Arg Leu Gln Cys Ala Arg Gly Phe Gly
            465                 470                 475                 480

Asp Trp Ile Asp Ser Ile Leu Ala Phe Ser Arg Ser Leu His Ser Leu
                            485                 490                 495

Leu Val Asp Val Pro Ala Phe Ala Cys Leu Ser Ala Leu Val Leu Ile
                        500                 505                 510

Thr Asp Arg His Gly Leu Gln Glu Pro Arg Arg Val Glu Glu Leu Gln
                    515                 520                 525

Asn Arg Ile Ala Ser Cys Leu Lys Glu His Val Ala Ala Val Ala Gly
                530                 535                 540

Glu Pro Gln Pro Ala Ser Cys Leu Ser Arg Leu Leu Gly Lys Leu Pro
            545                 550                 555                 560

Glu Leu Arg Thr Leu Cys Thr Gln Gly Leu Gln Arg Ile Phe Tyr Leu
                            565                 570                 575

Lys Leu Glu Asp Leu Val Pro Pro Pro Ile Ile Asp Lys Ile Phe
                        580                 585                 590

Met Asp Thr Leu Pro Phe
                    595

<210> SEQ ID NO 8
<211> LENGTH: 1797
<212> TYPE: DNA
<213> ORGANISM: Human

<400> SEQUENCE: 8
atgccctgta tccaagccca atatgggaca ccagcaccga gtccgggacc ccgtgaccac     60
ctggcaagcg accccctgac ccctgagttc atcaagccca ccatggacct ggccagcccc    120
gaggcagccc ccgctgcccc cactgccctg cccagcttca gcaccttcat ggacggctac    180
acaggagagt ttgacacctt cctctaccag ctgccaggaa cagtccagcc atgctcctca    240
gcctcctcct cggcctcctc cacatcctcg tcctcagcca cctcccctgc ctctgcttcc    300
ttcaagttcg aggacttcca ggtgtacggc tgctaccccg cccccctgag cggcccagtg    360
gatgaggccc tgtcctccag tggctctgac tactatggca cccctgctc ggccccgtcg    420 ccctccacgc ccagcttcca gccgccccag ctctctccct gggatggctc cttcggccac    480
ttctcgccca gccagactta cgaaggcctg cgggcatgga cagagcagct gcccaaagcc    540
tctgggcccc cacagcctcc agccttcttt ccttcagtc ctcccaccgg cccagccc     600 agcctggccc agagcccct gaagttgttc cctcacagg ccaccacca gctgggggag    660 ggagagagct attccatgcc tacggccttc ccaggtttgg cacccacttc tccacacctt    720
```

```
gagggctcgg ggatactgga tacacccgtg acctcaacca aggcccggag cggggcccca    780
ggtggaagtg aaggccgctg tgctgtgtgt ggggacaacg cttcatgcca gcattatggt    840
gtccgcacat gtgagggctg caagggcttc ttcaagcgca cagtgcagaa aaacgccaag    900
tacatctgcc tggctaacaa ggactgccct gtggacaaga gcggcgaaa ccgctgccag     960
ttctgccgct ccagaagtg cctggcggtg gcatggtga aggaagttgt ccgaacagac     1020
agcctgaagg gcggcgggg ccggctacct tcaaaaccca gcagccccc agatgcctcc    1080
cctgccaatc tcctcacttc cctggtccgt gcacacctgg actcagggcc cagcactgcc   1140
aaactggact actccaagtt ccaggagctg gtgctgcccc actttgggaa ggaagatgct   1200
ggggatgtac agcagttcta cgacctgctc tccggttctc tggaggtcat ccgcaagtgg   1260
gcggagaaga tccctggctt tgctgagctg tcaccggctg accaggacct gttgctggag   1320
tcggccttcc tggagctctt catcctccgc ctggcgtaca ggtctaagcc aggcgagggc   1380
aagctcatct tctgctcagg cctggtgcta caccggctgc agtgtgcccg tggcttcggg   1440
gactggattg acagtatcct ggccttctca aggtccctgc acagcttgct tgtcgatgtc   1500
cctgccttcg cctgcctctc tgcccttgtc tcatcaccg accggcatgg gctgcaggag   1560
ccgcggcggg tggaggagct gcagaaccgc atcgccagct gcctgaagga gcacgtggca   1620
gctgtggcgg cgagccccca gccagccagc tgcctgtcac gtctgttggg caaactgccc   1680
gagctgcgga ccctgtgcac ccagggcctg cagcgcatct tctacctcaa gctggaggac   1740
ttggtgcccc ctccacccat cattgacaag atcttcatgg acacgctgcc cttctga      1797

<210> SEQ ID NO 9
<211> LENGTH: 36
<212> TYPE: PRT
<213> ORGANISM: Human

<400> SEQUENCE: 9

Lys Asn Ala Lys Tyr Ile Cys Leu Ala Asn Lys Asp Cys Pro Val Asp
1               5                   10                  15

Lys Arg Arg Arg Asn Arg Cys Gln Phe Cys Arg Phe Gln Lys Cys Leu
            20                  25                  30

Ala Val Gly Met
        35

<210> SEQ ID NO 10
<211> LENGTH: 108
<212> TYPE: DNA
<213> ORGANISM: Human

<400> SEQUENCE: 10
aaaaacgcca agtacatctg cctggctaac aaggactgcc ctgtggacaa gaggcggcga     60
aaccgctgcc agttctgccg cttccagaag tgcctggcgg tgggcatg                 108

<210> SEQ ID NO 11
<211> LENGTH: 239
<212> TYPE: PRT
<213> ORGANISM: Human

<400> SEQUENCE: 11

Ser Ser Ala Asn Glu Asp Met Pro Val Glu Arg Ile Leu Glu Ala Glu
1               5                   10                  15

Leu Ala Val Glu Pro Lys Thr Glu Thr Tyr Val Glu Ala Asn Met Gly
            20                  25                  30

Leu Asn Pro Ser Ser Pro Asn Asp Pro Val Thr Asn Ile Cys Gln Ala
```

-continued

```
                 35                    40                    45
Ala Asp Lys Gln Leu Phe Thr Leu Val Glu Trp Ala Lys Arg Ile Pro
 50                     55                      60

His Phe Ser Glu Leu Pro Leu Asp Asp Gln Val Ile Leu Leu Arg Ala
 65                      70                     75                      80

Gly Trp Asn Glu Leu Leu Ile Ala Ser Phe Ser His Arg Ser Ile Ala
                         85                     90                      95

Val Lys Asp Gly Ile Leu Leu Ala Thr Gly Leu His Val His Arg Asn
                        100                    105                    110

Ser Ala His Ser Ala Gly Val Gly Ala Ile Phe Asp Arg Val Leu Thr
                        115                    120                    125

Glu Leu Val Ser Lys Met Arg Asp Met Gln Met Asp Lys Thr Glu Leu
                        130                    135                    140

Gly Cys Leu Arg Ala Ile Val Leu Phe Asn Pro Asp Ser Lys Gly Leu
145                                 150                    155                    160

Ser Asn Pro Ala Glu Val Glu Ala Leu Arg Glu Lys Val Tyr Ala Ser
                        165                    170                    175

Leu Glu Ala Tyr Cys Lys His Lys Tyr Pro Glu Gln Pro Gly Arg Phe
                        180                    185                    190

Ala Lys Leu Leu Leu Arg Leu Pro Ala Leu Arg Ser Ile Gly Leu Lys
                        195                    200                    205

Cys Leu Glu His Leu Phe Phe Phe Lys Leu Ile Gly Asp Thr Pro Ile
210                                 215                    220

Asp Thr Phe Leu Met Glu Met Leu Glu Ala Pro His Gln Met Thr
225                                 230                    235

<210> SEQ ID NO 12
<211> LENGTH: 21
<212> TYPE: RNA
<213> ORGANISM: Human

<400> SEQUENCE: 12
aagcacuaug gaguguacag c                                                     21
```